(12) United States Patent
Okandan et al.

(10) Patent No.: US 9,907,496 B1
(45) Date of Patent: Mar. 6, 2018

(54) OPTOELECTRONIC SYSTEM AND APPARATUS FOR CONNECTION TO BIOLOGICAL SYSTEMS

(71) Applicant: National Technology & Engineering Solutions of Sandia, LLC, Albuquerque, NM (US)

(72) Inventors: Murat Okandan, Edgewood, NM (US); Gregory N. Nielson, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 514 days.

(21) Appl. No.: 14/314,176

(22) Filed: Jun. 25, 2014

Related U.S. Application Data

(60) Provisional application No. 61/839,264, filed on Jun. 25, 2013.

(51) Int. Cl.
*A61B 5/1455* (2006.01)
*A61B 5/1459* (2006.01)
*A61B 5/1473* (2006.01)

(52) U.S. Cl.
CPC .......... *A61B 5/1459* (2013.01); *A61B 5/1473* (2013.01); *A61B 2560/0214* (2013.01)

(58) Field of Classification Search
None
See application file for complete search history.

(56) References Cited

U.S. PATENT DOCUMENTS

| | | | |
|---|---|---|---|
| 4,892,538 A | 1/1990 | Aebischer et al. | |
| 5,339,051 A * | 8/1994 | Koehler | H03H 9/1035 310/318 |
| 5,474,547 A | 12/1995 | Aebischer et al. | |
| 5,994,911 A | 11/1999 | Fonash et al. | |
| 6,330,464 B1 * | 12/2001 | Colvin, Jr. | A61B 5/0031 128/903 |
| 6,348,806 B1 | 2/2002 | Okandan et al. | |
| 6,445,939 B1 | 9/2002 | Swanson et al. | |

(Continued)

FOREIGN PATENT DOCUMENTS

WO WO 2010/042750 A2 4/2010

OTHER PUBLICATIONS

Abaya TVF et al., "Characterization of a 3D optrode array for infrared neural stimulation," *Biomed. Optics Exp.* Sep. 2012;3(9):2200-19.

(Continued)

*Primary Examiner* — Eric Winakur
*Assistant Examiner* — Marjan Fardanesh
(74) *Attorney, Agent, or Firm* — Martin I. Finston; Helen S. Baca

(57) ABSTRACT

The present invention relates to a biological probe structure, as well as apparatuses, systems, and methods employing this structure. In particular embodiments, the structure includes a hermetically sealed unit configured to receive and transmit one or more optical signals. Furthermore, the structure can be implanted subcutaneously and interrogated externally. In this manner, a minimally invasive method can be employed to detect, treat, and/or assess the biological target. Additional methods and systems are also provided.

26 Claims, 14 Drawing Sheets

(56) References Cited

U.S. PATENT DOCUMENTS

| | | | |
|---|---|---|---|
| 6,535,671 | B1 | 3/2003 | Poole |
| 6,537,437 | B1 | 3/2003 | Galambos et al. |
| 6,564,087 | B1 | 5/2003 | Pitris et al. |
| 6,645,757 | B1 | 11/2003 | Okandan et al. |
| 6,662,039 | B2 | 12/2003 | Yuste et al. |
| 6,797,187 | B1 | 9/2004 | Galambos et al. |
| 7,004,198 | B1 | 2/2006 | Okandan et al. |
| 7,127,301 | B1 | 10/2006 | Okandan et al. |
| 7,246,524 | B1 | 7/2007 | Kholwadwala et al. |
| 7,291,003 | B1 | 11/2007 | Okandan et al. |
| 7,308,317 | B1 | 12/2007 | Okandan et al. |
| 7,341,222 | B1 | 3/2008 | Reuel et al. |
| 7,540,469 | B1 | 6/2009 | Okandan |
| 7,727,314 | B1 | 6/2010 | Manginell et al. |
| 7,729,773 | B2 | 6/2010 | Sloan |
| 7,773,840 | B2 | 8/2010 | Kwakernaak et al. |
| 7,826,065 | B1 | 11/2010 | Okandan et al. |
| 7,979,105 | B2 | 7/2011 | Kipke et al. |
| 8,000,804 | B1 | 8/2011 | Wessendorf et al. |
| 8,205,497 | B1 | 6/2012 | Okandan et al. |
| 8,285,394 | B1 | 10/2012 | Wessendorf et al. |
| 8,323,955 | B1 | 12/2012 | Okandan |
| 8,329,503 | B1 | 12/2012 | Nielson et al. |
| 8,349,547 | B1 | 1/2013 | Burckel et al. |
| 8,357,187 | B1 | 1/2013 | Bendett et al. |
| 8,398,692 | B2 | 3/2013 | Deisseroth et al. |
| 8,592,249 | B1 | 11/2013 | Nielson et al. |
| 8,603,790 | B2 | 12/2013 | Deisseroth et al. |
| 8,614,395 | B1 | 12/2013 | Nielson et al. |
| 8,674,689 | B1 | 3/2014 | Nielson et al. |
| 8,680,810 | B1 | 3/2014 | Okandan et al. |
| 8,696,722 | B2 | 4/2014 | Deisseroth et al. |
| 8,726,730 | B1 | 5/2014 | Nielson et al. |
| 8,728,857 | B1 | 5/2014 | Nielson et al. |
| 8,729,673 | B1 | 5/2014 | Okandan et al. |
| 8,736,108 | B1 | 5/2014 | Nielson et al. |
| 2009/0118800 | A1 | 5/2009 | Deisseroth et al. |
| 2009/0177144 | A1 | 7/2009 | Masmanidis et al. |
| 2009/0210039 | A1 | 8/2009 | Boyden et al. |
| 2009/0326384 | A1 | 12/2009 | Bigio et al. |
| 2010/0292931 | A1 | 11/2010 | Wang et al. |
| 2011/0024771 | A1 | 2/2011 | Hajj-Hassan et al. |
| 2012/0287420 | A1 | 11/2012 | McLaughlin et al. |
| 2012/0323288 | A1 | 12/2012 | Anderson et al. |
| 2013/0030274 | A1 | 1/2013 | Jamieson et al. |
| 2013/0039616 | A1 | 2/2013 | Shambat et al. |
| 2013/0079615 | A1 | 3/2013 | Yoon et al. |
| 2013/0085398 | A1 | 4/2013 | Roukes |
| 2013/0224756 | A1 | 8/2013 | Cohen et al. |
| 2013/0245725 | A1 | 9/2013 | Mahdevan-Jansen et al. |
| 2013/0269747 | A1 | 10/2013 | Lentine et al. |
| 2014/0024902 | A1 | 1/2014 | Mahadevan-Jansen et al. |
| 2014/0060616 | A1 | 3/2014 | Okandan et al. |
| 2014/0084450 | A1 | 3/2014 | Nielson et al. |
| 2014/0094674 | A1 | 4/2014 | Nurmikko et al. |
| 2014/0102520 | A1 | 4/2014 | Tauke-Pedretti et al. |
| 2014/0142664 | A1 | 5/2014 | Roukes et al. |

OTHER PUBLICATIONS

Accoto D et al., "An implantable neural interface with electromagnetic stimulation capabilities," *Med. Hypoth.* 2013;81:322-7.
Anand S et al., "Electrothermal microactuators with peg drive improve performance for brain implant applications," *J. Microelectromech. Sys.* Oct. 2012;21(5):1172-86.
Anderson RR et al., "The optics of human skin," *J. Invest. Dermatol.* 1981;77:13-9.
Arrigan DWM, "Nanoelectrodes, nanoelectrode arrays and their applications," *Analyst* 2004;129:1157-65.
Brady GP et al., "Recent developments in optical fibre sensing using fibre Bragg gratings," *Proc. SPIE* Oct. 1996;2839:8-19.
Carboni C, "Electronic bidirectional interfaces to the peripheral nervous system for prosthetic applications," *Electronic and Computer Engineering Ph.D. thesis in the Department of Electrical and Electronic Engineering at the University of Cagliari*, Mar. 2012 (135 pp.).
Chen R et al., "Nanolasers grown on silicon," *Nature Photon.* Mar. 2011;5:170-5.
Cheng HD et al., "Monolithic bi-directional linear microactuator for light beam manipulation," *IEEE/LEOS Int'l Conf. on Optical MEMS and Their Applications*, held on Aug. 21-24, 2006 in Big Sky, MT, pp. 122-123.
Chiu Y et al., "MEMS-based miniature optical pickup," *IEEE Trans. Magn.* Feb. 2005;41(2):967-70.
Chung K et al., "Clarity for mapping the nervous system," *Nature Methods* Jun. 2013;10(6):508-13.
Chung K et al., "Structural and molecular interrogation of intact biological systems," *Nature* May 2013;497:332-7.
Cipriani C et al., "Objectives, criteria and methods for the design of the SmartHand transradial prosthesis," *Robotica* 2010;28:919-27.
Cipriani C et al., "The SmartHand transradial prosthesis," *J. Neuroeng. Rehab.* May 2011;8:29 (13 pp.).
Cowan WD et al., "Integrated FET-polysilicon micromachining process for optical MEMS," *Proc. IEEE/LEOS Int'l Conf. Optical MEMS & their Applications*, held on Aug. 21-24, 2006 in Big Sky, MT, pp. 64-65.
Cristea D et al., "Integrated optics on silicon for sensor applications," *Proc. 9th Mediterranean Electrotechnical Conf.*, held on May 18-20, 1998 in Tel-Aviv, vol. 2, pp. 1444-1448.
Cristea D et al., "Silicon opto-FET coupled to waveguides for integrated optical microsystems," *Proc. SPIE*, held on Sep. 16, 1998 in Beijing, China, vol. 3551, pp. 63-74.
Cruz-Campa JL et al., "Back-contacted and small form factor GaAs solar cell," *Proc. 35th IEEE Photovoltaic Specialists Conf. (PVSC)*, held on Jun. 20-25, 2010 in Honolulu, HI, pp. 1248-1252.
Cruz-Campa JL et al., "Fabrication of lattice mismatched multijunction photovoltaic cells using 3D integration concepts," *Proc. 38th IEEE PVSC*, held on Jun. 3-8, 2012 in Austin, TX, pp. 932-936.
Cruz-Campa JL et al., "Microlens rapid prototyping technique with capability for wide variation in lens diameter and focal length," *Microelectron. Eng.* Nov. 2010;87(11):2376-81.
Cruz-Campa JL et al., "Microsystems enabled photovoltaics: 14.9% efficient 14 μm thick crystalline silicon solar cell," *Sol. Energy Mater. Sol. Cells* Feb. 2011;95(2):551-8.
Cruz-Campa JL et al., "Ultra-thin single crystal silicon modules capable of 450 W/kg and bending radii <1mm: Fabrication and characterization," *Proc. 39th IEEE PVSC*, held on Jun. 16-21, 2013 in Tampa, FL, pp. 1216-1223.
Cruz-Campa JL et al., "Ultrathin and flexible single crystal silicon mini-modules," *Proc. 27th European Photovoltaic Solar Energy Conf. and Exhibition*, held on Sep. 22-23, 2012 in Frankfurt, Germany, pp. 2203-2206.
Cruz-Campa JL et al., "Ultrathin and micro-sized solar cell performance optimization via simulations," *Prog. Photovolt. Res. Appl.* 2013;21:1114-26.
Cruz-Campa JL et al., "Ultrathin flexible crystalline silicon: Microsystems-enabled photovoltaics," *IEEE J. Photovolt.* Jul. 2011;1(1):3-8.
Deisseroth K et al., "Engineered approaches to illuminating brain structure and dynamics," *Neuron* Oct. 2013;80:568-77.
Di Pino G et al., "In human implant of intraneural multielectrodes for controlling a 5-fingered hand prosthesis and delivering sensorial feedback," Chapter 3, pp. 28-38 in *Grasping the Future: Advances in Powered Upper Limb Prosthetics*, eds. V.P. Castelli and M. Troncossi, 2012, Bentham Science Publishers, Oak Park, IL.
Di Pino G, "Bidirectional peripheral-nerve interfaces for hand prosthesis control: In human validation and analysis of the induced neuroplasticity and of the foreign body reaction," *Biomedical Engineering Ph.D. thesis in the School of Engineering at the Università Campus Bio-Medico di Roma*, Jan. 2010 (137 pp.).
Draper B et al., "Radiation response of a gate-all-around silicon nano-wire transistor," *IEEE Trans. Nucl. Sci.* Nov. 2009;56(6):3274-9.

(56) References Cited

OTHER PUBLICATIONS

El-Fatatry A, "Optical microsystems, mechano-optical-electro-mechanical systems—MOEMS," in *MEMS Aerospace Applications*, Feb. 2004 (79 pp.), NATO Science and Technology Organization (Ref. No. RTO-EN-AVT-105).

Ercole F et al., "Photo-responsive systems and biomaterials: photochromic polymers, light-triggered self-assembly, surface modification, fluorescence modulation and beyond," *Polym. Chem.* 2010;1:37-54.

Garrigues M et al., "III-V semiconductor based MOEMS devices for optical telecommunications," *Microelectron. Eng.* 2002;61-62:933-45.

Gupta V et al., "Microsystems-enabled photovoltaics: A path to the widespread harnessing of solar energy," *Future Photovolt.* May 2010 (9 pp.).

Hall NA et al., "Surface and bulk-silicon-micromachined optical displacement sensor fabricated with the SwIFT-Lite™ process," *J. Microelectromech. Sys.* Aug. 2006;15(4):770-6.

Hassler C et al., "Polymers for neural implants," *J. Polym. Sci. B Polym. Phys.* 2011;49:18-33.

Hocevar M et al., "Growth and optical properties of axial hybrid III-V/silicon nanowires," *Nature Commun.* Dec. 2012;3:1266 (6 pp.).

Huang CW et al., "Electrochemical detection of the neurotransmitter dopamine by nanoimprinted interdigitated electrodes and a CMOS circuit with enhanced collection efficiency," *IEEE Sensors J.* Sep. 2011;11(9):1826-31.

Jackson N et al., "Long-term cortical recordings with microactuated microelectrodes," *Proc. 3rd Int'l IEEE/EMBS Conf. Neural Eng.*, held on May 2-5, 2007 in Kohala Coast, HI, pp. 141-143.

Jackson N et al., "Long-term neural recordings using MEMS based movable microelectrodes in the brain," *Front. Neuroeng.* Jun. 18, 2010;3:10 (13 pp.).

Jackson N et al., "Nonhermetic encapsulation materials for MEMS-based movable microelectrodes for long-term implantation in the brain," *J. Microelectromech. Syst.* Jan. 1, 2009;18(6):1234-45.

James CD et al., "Surface micromachined dielectrophoretic gates for the front-end device of a biodetection system," *J. Fluids Eng.* Apr. 2005;128(1):14-9.

Jared BH et al., "Efficient micro-concentrator for microsystems-enabled photovoltaics," Abstract for the *29th Am. Soc. Precision Eng. Annual Meeting*, held on Nov. 13, 2014 in Boston, MA (2 pp.)(available at http://www.aspe.net/publications/Short%20Abstracts%2014A/4120.pdf, last accessed Jun. 16, 2014).

Jared BH et al., "Micro-concentrators for a microsystems-enabled photovoltaic system," *Opt. Express* Mar. 10, 2014;22 Suppl 2:A521-7.

Justice J et al., "Wafer-scale integration of group III-V lasers on silicon using transfer printing of epitaxial layers," *Nature Photon.* Sep. 2012;6:610-4.

Kang YT et al., "Evaluating biocompatibility of semiconductive gallium nitride, flat and nano-structured silicon chips by cell viability, adhesion and growth," *Int'l Nanoelectronics Conf.*, held on Jan. 3-8, 2010 in Hong Kong, pp. 811-812.

Kim TI et al., "Injectable, cellular-scale optoelectronics with applications for wireless optogenetics," *Science* Apr. 2013;340:211-6.

Kim TI et al., Supplementary Materials for "Injectable, cellular-scale optoelectronics with applications for wireless optogenetics," *Science* Apr. 2013;340:211-6, available at sciencemag.org/cgi/content/full/340/6129/211/DC1 (42 pp.).

Larsson KC et al., "Organic bioelectronics for electronic-to-chemical translation in modulation of neuronal signaling and machine-to-brain interfacing," *Biochim. Biophys. Acta* 2013;1830:4334-44.

Lentine AL et al., "Optimal cell connections for improved shading, reliability, and spectral performance of microsystem enabled photovoltaic (MEPV) modules," *Proc. 35th IEEE PVSC*, held on Jun. 20-25, 2010 in Honolulu, HI, pp. 3048-3054.

Li Y et al., "Thermal analysis of injectable, cellular-scale optoelectronics with pulsed power," *Proc. R. Soc. A* 469:20130142 (13 pp.).

Mattis J et al., "Principles for applying optogenetic tools derived from direct comparative analysis of microbial opsins," *Nature Methods* Feb. 2012;9(2):159-172 (including 3 pp. of Online Methods).

McCall JG et al., "Fabrication and application of flexible, multimodal light-emitting devices for wireless optogenetics," *Nature Protoc.* 2013;8(12):2413-28.

Micera S et al., "Control of hand prosthesis using peripheral information," *IEEE Rev. Biomed. Eng.* 2010;3:48-68.

Muller R et al., "3D microstructures integrated with optical waveguides and photodiodes on silicon," *Proc. 9th Mediterranean Electrotechnical Conf.*, held on May 18-20, 1998 in Tel-Aviv, vol. 1, pp. 392-395.

Muthuswamy J et al., "A chronic micropositioning system for neurophysiology," *Proc. 2nd Joint Eng. Med. Biol. Soc./Biomed. Eng. Soc. (EMBS/BMES) Conf.*, held on Oct. 23-26, 2002 in Houston, TX, vol. 3, pp. 2115-2116.

Muthuswamy J et al., "An array of microactuated microelectrodes for monitoring single-neuronal activity in rodents," *IEEE Trans. Biomed. Eng.* Aug. 2005;52(8):1470-7.

Muthuswamy J et al., "Electrostatic microactuators for precise positioning of neural microelectrodes," *IEEE Trans. Biomed. Eng.* Oct. 2005;52(10):1748-55.

Muthuswamy J et al., "Implantable microtechnologies for the brain: Challenges and strategies for reliable operation," *Proc. IEEE Int'l Reliability Physics Symposium (IRPS)*, held on Apr. 10-14, 2011 in Monterey, CA, pp. 3B.2.1-3B.2.4.

Muthuswamy J et al., "Microactuated neural probes to compensate for brain micromotion," *Proc. 25th Annual Int'l Conf. IEEE Eng. Med. Biol. Soc.*, held on Sep. 17-21, 2003, vol. 2, pp. 1941-1943.

Muthuswamy J et al., "Movable microprobes for the brain," *Proc. 3rd IEEE/EMBS Special Topic Conf. Microtechnol. Med. Biol.*, held on May 12-15, 2005 in Oahu, HI, pp. 86-87.

Muthuswamy J et al., "Single neuronal recordings using surface micromachined polysilicon microelectrodes," *J. Neurosci. Methods* Mar. 15, 2005;142(1):45-54.

Muthuswamy J et al., "Surface micro-machined polysilicon probes for neurophysiology," *Proc. 22nd Annual Int'l Conf. IEEE Eng. Med. Biol. Sci.*, held on Jul. 23-28, 2000 in Chicago, IL, p. 259.

Natarajan CM et al., "Superconducting nanowire single-photon detectors: Physics and applications," *Supercond. Sci. Technol.* 2012;25:063001 (16 pp.).

Nielson GN et al., "216 cell microconcentrator module with moderate concentration, ±4° acceptance angle, and 13.3 mm focal length," *Proc. 39th IEEE PVSC*, held on Jun. 16-21, 2013 in Tampa, FL, pp. 465-469.

Nielson GN et al., "Leveraging scale effects to create next-generation photovoltaic systems through micro- and nanotechnologies," *Proc. SPIE* May 2012;8373:837317 (10 pp.).

Nielson GN et al., "Microfabrication of microsystem-enabled photovoltaic (MEPV) cells," *Proc. SPIE* Feb. 2011;7927:79270P (12 pp.).

Nielson GN et al., "Microscale c-Si (C)PV cells for low-cost power," *Proc. 34th IEEE PVSC*, held on Jun. 7-12, 2009 in Philadelphia, PA, pp. 1816-1821.

Nielson GN et al., "Microscale PV cells for concentrated PV applications," *24th European Photovoltaic Solar Energy Conf. and Exhibition*, held on Sep. 21-25, 2009 in Hamburg, Germany, pp. 170-173 (3 pp.).

Nielson GN et al., "Next generation photovoltaic cells and systems through MEMS technology," *ECS Trans.* 2012;44(1):1347-52.

Ohira K et al., "On-chip optical interconnection by using integrated III-V laser diode and photodetector with silicon waveguide," *Opt. Express* Jul. 2010;18(15):15440-7.

Okandan M et al., "High speed (GHz), ultra-high pressure (GPA) sensor array fabricated in integrated CMOS+MEMS process," *Proc. IEEE 22nd Int'l Conf. Micro Electro Mech. Sys.*, held on Jan. 25-29, 2009 in Sorrento, Italy, pp. 845-847.

Okandan M et al., "Micromachined patch clamp array," *SAND Technical Report No. SAND2002-0925*, Jun. 2002, 18 pp.

Okandan M et al., "Patch-clamp array with on-chip electronics, optics, flow control and mechanical actuation," *Proc. 7th Int'l Conf.*

(56) References Cited

OTHER PUBLICATIONS on Miniaturized Chem. Biochem. Anal. Sys., held on Oct. 5-9, 2003 in Squaw Valley, CA, pp. 1037-1040.

Paap S et al., "Cost analysis for flat-plate concentrators employing microscale photovoltaic cells," *Proc. 39th IEEE PVSC*, held on Jun. 16-21, 2013 in Tampa, FL, pp. 3431-3434.

Passaro VMN et al., "Wavelength interrogator for optical sensors based on a novel thermo-optic tunable filter in SOI," *J. Lightwave Technol.* Jul. 2012;30(13):2143-50.

Rodak LE et al., "Light emitting diode growth on curved gallium nitride surfaces," *Mater. Res. Soc. Symp. Proc.* 2011;1288:DOI: 10.1557/opl.2011.286 (6 pp.).

Rossini PM et al., "Double nerve intraneural interface implant on a human amputee for robotic hand control," *Clin. Neurophysiol.* 2010;121:777-83.

Sandia National Laboratories, "Microsystems enabled photovoltaics (MEPV) 'Solar Glitter'," Sandia Ref. No. SAND 2012-0430P, 2012 (1 p.).

Seo D et al., "Neural dust: An ultrasonic, low power solution for chronic brain-machine interfaces," arXiv:1307.2196v1 [q-bio.NC], Jul. 2013 (11 pp., available at arxiv.org/pdf/1307.2196.pdf).

Sheng Z et al., "InGaAs PIN photodetectors integrated on silicon-on-insulator waveguides," *Opt. Express* Jan. 2010;18(2):1756-61.

Shi W et al., "Silicon photonic Bragg-grating couplers for optical communications," *Proc. SPIE* Feb. 2014;9010:90100F (12 pp.).

Smedemark-Margulies N et al., "Tools, methods, and applications for optophysiology in neuroscience," *Front. Molec. Neurosci.* Jul. 2013;6:18 (13 pp.).

Sparks JR et al., "Templated chemically deposited semiconductor optical fiber materials," *Annu. Rev. Mater. Res.* 2013;43:527-57.

Stieglitz T et al., "Miniaturized neural interfaces and implants," *Proc. SPIE* 2012; 8251:82510A (12 pp.).

Sweatt W et al., "Concentrating Photovoltaic systems using micro-optics," *Optics for Solar Energy Conf.*, held on Nov. 2-3, 2011 in Austin, TX (3 pp.).

Sweatt W et al., "Micro-optics for high-efficiency optical performance and simplified tracking for concentrated photovoltaics (CPV)," *Int'l Optical Design Conf.*, held on Jun. 13-17, 2010 in Jackson Hole, WY (8 pp.).

Sweatt WC et al., "Photo-voltaic system using micro-optics," *Optics for Solar Energy Conf.*, held on Nov. 11-14, 2012 in Eindhoven, the Netherlands (3 pp.).

Szymański W et al., "Reversible photocontrol of biological systems by the incorporation of molecular photoswitches," *Chem. Rev.* 2013;113:6114-78.

Tamura K et al., "A glass-coated tungsten microelectrode enclosing optical fibers for optogenetic exploration in primate deep brain structures," *J. Neurosci. Methods* 2012;211:49-57.

Tauke-Pedretti A et al., "Resistance considerations for stacked small multi-junction photovoltaic cells," *Proc. 39th IEEE PVSC*, held on Jun. 16-21, 2013 in Tampa, FL, pp. 2131-2135.

Thacker HD et al., "Hybrid integration of silicon nanophotonics with 400nm-CMOS VLSI drivers and receivers," *IEEE Electronic Components and Technology Conf.*, held on May 31, 2011 to Jun. 3, 2011 at Lake Buena Vista, FL, pp. 829-835.

Tuchin VV, "Light scattering study of tissues," *Phys. Uspekhi* 1997;40(5):495-515.

Vahala KJ, "Optical microcavities," *Nature* Aug. 2003;424:839-46.

Van Thourhout D et al., "Nanophotonic devices for optical interconnect," *IEEE J. Sel. Top. Quantum Electron.* Sep./Oct. 2010;16(5):1363-75.

Wu MC, "Micromachining for optical and optoelectronic systems," *Proc. IEEE* Nov. 1997;85(11):1833-56.

Yang BB et al., "Failure analysis techniques for microsystems-enabled photovoltaics," *IEEE J. Photovolt.* Jan. 2014;4(1):470-6.

Zhang C et al., "Broadband optical fiber tap based on cladding-mode coupling," *Opt. Eng.* Jul. 2012;51(7):075001 (6 pp.).

Zhu L et al., "Fiber-coupled light-emitting diode with a capillary-bonded hemispherical lens," *IEEE Photon. Technol. Lett.* Dec. 2011;23(24):1857-9.

Ziaei-Moayyed M et al., "Gate-all-around single-crystalline silicon nanowire optical.sensor," *Proc. 16th Int'l Solid-State Sens. Actuat. Microsys. Conf. (Transducers)*, held on Jun. 5-9, 2011 in Beijing, China, pp. 1757-1760.

\* cited by examiner

OPTOELECTRONIC SYSTEM AND APPARATUS FOR CONNECTION TO BIOLOGICAL SYSTEMS

CROSS-REFERENCE TO RELATED APPLICATION

This application claims the benefit of U.S. Provisional Application No. 61/839,264, filed Jun. 25, 2013, which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to optoelectronic structures capable of connecting to biological systems. In particular, the structures of the invention include a hermetically sealed unit configured to receive and transmit one or more optical and/or electrical signals. These structures are configured to be coupled optically to one or more components to allow an implanted structure to be interrogated externally (e.g., by way of an external transceiver unit). Additional devices, apparatuses, systems, and methods including such optoelectronic structures are also provided.

BACKGROUND OF THE INVENTION

In recording and stimulating neurons either in the peripheral or central nervous system, electrophysiological methods (e.g., neural probes, patch clamp measurements, etc.) are the gold standard. However, these methods are limited in spatial and temporal characteristics. For instance, some probes are large (e.g., on a millimeter scale) and, therefore, lack spatial precision in either stimulating or detecting individual neurons or isolated regions within neural tissue. In another instance, some probes can be difficult to implant and maintain without complications and degradation both in the target tissue and within the biological system. Accordingly, new probes and apparatuses having such spatio-temporal control are desired. In particular, systems employing such probes would be beneficial for biological links between the nervous system and an external unit (e.g., a prosthetic for an amputated limb).

Furthermore, current developments in optogenetics have opened up the possibility of studying neurons and neuronal networks in vivo. In optogenetics, light sensitive ion channels or other molecules are expressed in transfected, genetically engineered cells, such that directed optical signals can be used to selectively activate or stimulate these engineered cells. Thus, new tools and methods to enable in vivo studies while minimizing invasive procedures would be beneficial.

SUMMARY OF THE INVENTION

The present invention relates to a biological probe structure (e.g., an active structure), as well as apparatuses, systems, and methods employing this structure. Such structures include optoelectronic features capable of connecting to biological systems. In particular embodiments, the structure includes a hermetically sealed unit configured to receive and transmit one or more optical and/or electrical signals. These structures are configured to be coupled optically to one or more components (e.g., an optical connector and/or an optical collector). Furthermore, the structure can be implanted subcutaneously and interrogated externally (e.g., by way of an external transceiver unit). In this manner, a minimally invasive method can be employed to detect, treat, and/or assess the biological target. Additional methods and systems are also provided.

The present invention features a biological probe structure including a hermetically sealed unit. In some embodiments, the unit includes: one or more emitters, where at least one emitter is configured to transmit a target input to a biological target and where the target input is a first optical and/or electrical signal; one or more detectors, where at least one detector is configured to receive a target output from the biological target and where the target output is a second optical and/or electrical signal; and a signal processing circuitry coupled electrically to the one or more emitters and the one or more detectors.

In some embodiments, the circuitry is configured to receive one or more electrical signals from at least one detector, apply an algorithm to the electrical signal(s) to provide one or more processed electrical signals, and/or transmit the processed electrical signal(s) to at least one emitter. In one embodiment, the emitter is configured to convert the processed electrical signal(s) to the target input for transmission to the biological target. In another embodiment, the circuitry is configured within or on a substrate having a peripheral surface and a medial surface, where one or more emitters and/or detectors (e.g., as an array) are disposed on the peripheral surface.

In some embodiments, the structure is a self-contained structure configured to be embedded in a target region. In further embodiments, the structure is configured to transmit the one or more target inputs directly into the target region and to receive one or more target outputs directly from the same target region.

In some embodiments, the biological probe structure includes an optical connector (e.g., an optical fiber) connected optically to the hermetically sealed unit. In other embodiments, the biological probe structure further includes an optical collector connected to a proximal end of the optical connector and the hermetically sealed unit connected to a distal end of the optical connector.

The invention also features an apparatus including an optical connector having a proximal end and a distal end; and a plurality of coupling nodes (e.g., any described herein). In some embodiments, each coupling node includes one or more biological probe structures (e.g., any described herein), and each coupling node is connected optically to the distal end of the connector. In some embodiments, the optical connector is configured to transmit an external optical input to the coupling node(s) and to receive one or more relayed optical outputs from the coupling node(s).

In other embodiments, the apparatus includes two or more optical connectors. In some embodiments, the apparatus includes a first optical connector that includes a plurality of first coupling nodes and a second optical connector that includes a plurality of second coupling nodes. In some embodiments, at least one first coupling node is configured to communicate electrically and/or optically with at least one second coupling node.

In some embodiments, the apparatus further includes an optical collector (e.g., a lens configured to receive one or more external optical inputs from an external transceiver unit) connected optically to the proximal end of the connector. In further embodiments, a reflector is disposed on a surface of the collector.

In some embodiments, the optical connector includes an internal scattering structure (e.g., a Bragg structure) or an optical tap configured to provide split an external optical input into one or more optical input signals. In other embodiments, each coupling node is arrayed along the optical connector near the scattering structure or tap, such that a portion of the light incident on each scattering structure or tap is coupled into a corresponding coupling node.

In another aspect, the invention features a system for connecting to a biological target, the system including an apparatus (e.g., any described herein) and an external transceiver unit. In some embodiments, the external transceiver unit is configured to transmit one or more external optical inputs to the apparatus and configured to receive one or more injected optical outputs from the apparatus. In other embodiments, the system further includes a prosthetic configured to house the external transceiver unit.

In some embodiments, the system further includes a power unit configured to be connected to the external transceiver unit. In other embodiments, the system includes a processing unit configured to be connected to the power unit.

In yet another aspect, the invention features a method of detecting and/or treating a biological target, the method including: providing one or more external optical inputs to an apparatus (e.g., any described herein). In some embodiments, the apparatus is located in a target region of the biological target, thereby activating one or more coupling nodes of the apparatus to detect and/or treat the biological target.

In another aspect, the invention features a method of detecting and/or treating a biological target, the method including: providing one or more external optical inputs to one or more biological probe structures (e.g., any described herein), where the structures are located in a target region of the biological target, thereby activating one or more emitters and/or detectors of the structure to detect and/or treat the biological target.

In any method herein, the method can include, prior to the providing step, injecting the one or more biological probe structures or apparatus into the target region.

In any method herein, the method can further include receiving one or more injected optical outputs transmitted from the one or more biological probe structures or apparatus. In other embodiments, an external transceiver unit is configured to transmit the external optical input(s) to the one or more biological probe structures or apparatus; and to receive the injected optical output(s) from the one or more biological probe structures or apparatus.

In any of the embodiments herein, the biological target includes any useful target or target region, such as a tissue (e.g., neural tissue, neural fascicles, subcutaneous tissue, muscle, nerve, peripheral nerve, central nerve, etc.), a cell (e.g., a neuron, a muscle cell, or a glial cell), an organ (e.g., brain), or a subcutaneous region of a subject (e.g., a human subject).

In any embodiments herein, the structure, apparatus, system, or method includes an ionic layer and/or a modulation layer disposed on a peripheral surface of a surface (e.g., of the hermetically sealed unit and/or coupling nodes). In some embodiments, the ionic layer and/or the modulation layer includes a light-activated material, an optically interrogatable material, a detection material, or a photoemissive material. In yet other embodiments, the ionic layer and/or the modulation layer includes a material configured to alter and/or detect a local ionic and/or local modulator concentration upon activation. In some embodiments, activation includes stimulating and/or suppressing cellular activity in the target region.

In any embodiment herein, the structure, apparatus, system, or method includes one or more power photodetectors. In some embodiments, the power photodetector(s) are configured to provide internal electrical power to the hermetically sealed unit and/or coupling node. In further embodiments, the power photodetector(s) are configured to power the signal processing circuitry.

In any embodiment herein, the biological probe structure, connector, collector, or apparatus is configured for in vivo implantation or injection in a target region.

In any embodiment herein, the apparatus, system, or method further includes an external transceiver unit configured to receive and transmit transcutaneous signals to and from the collector, apparatus, and/or structure.

Definitions

As used herein, the term "about" means+/−10% of any recited value. As used herein, this term modifies any recited value, range of values, or endpoints of one or more ranges.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

The present invention features a system that provides an implantable, completely insulated system that does not expose any non-beneficial electrical connections to the tissue, either on external surfaces or encased within polymeric substrates of the system. Non-beneficial (e.g., non-therapeutic) electrochemical reactions can lead to degradation of the interconnections, and exposed electrodes in conventional neural probes can ultimately limit the lifetime and applicability of such systems. Power and data are delivered and extracted from the system through optical coupling, either through a fiber or free-space means. This allows an external unit (e.g., an external transceiver unit) to provide the needed power and telemetry needs for the experiment and/or medical application.

Figure 1A:
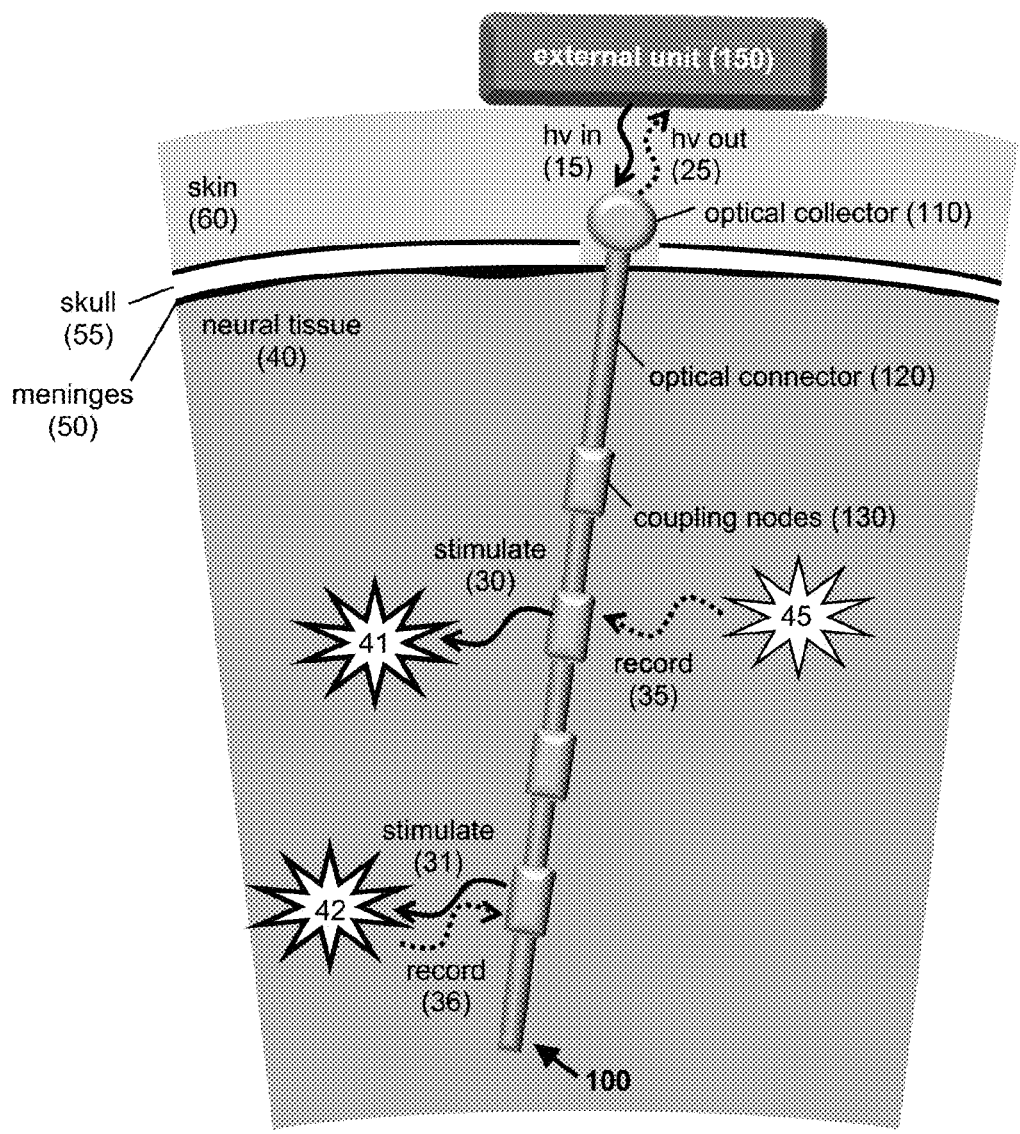
FIG. 1A-1E provides schematics of an apparatus 100 including a plurality of coupling nodes 130, where each node can include one or more active structures 136. Provided are (A) a partially schematic, cutaway drawing depicting an exemplary embodiment of an apparatus 100 embedded subcutaneously in a human or another in vivo biological system, (B) a cross-sectional view of an exemplary coupling node, and (C) a schematic of exemplary geometries for coupling nodes 133, 134/135, 137, 138. Also provided are schematics showing (D) input signals transmitted to the target 40 and (E) output signals transmitted from the target 40.

FIG. 1A shows an exemplary system including an apparatus 100 and an external unit 150. As can be seen, an optical connector 120 (e.g., an optical fiber) terminated by an optical collector 110 is embedded subcutaneously in a human being or other in vivo biological system. An external optical transceiver unit 150 transmits and receives light 15, 25 for transcutaneous coupling to the optic collector 110.

Arrayed along the optical connector 120 is a system of coupling nodes 130, each of which is capable of transmitting an optical or electrical signal 30, 31 into the surrounding biological tissue (e.g., neural tissue 40) and receiving an optical or electrical signal therefrom 35, 36. In the figure, the biological structures that are targets for the transmitted signal, and those that are sources of the received signal, are depicted for purposes of illustration but not limitation as neurons 41, 42, 45. The apparatus can be embedded in the target area to allow transcutaneous access to the optical collector (e.g., by locating the collector 110 under the skin layer 60 but above the skull 55 and meninges 50) but permit the coupling nodes to stimulate, record, and/or detect one or more biological targets (e.g., by locating the distal end of the connector within the neural tissue 40 and in proximity to one or more neurons 41, 42, 45). Details of each component of the apparatus follow.

Coupling Node

The apparatus generally includes one or more coupling nodes. The coupling node allows an external optical input to be relayed to the biological target. In general, the coupling node includes an active structure (e.g., any described herein) that is coupled optically to the optical connector. In an alternative embodiment, the system can be realized without optical connector or fibers, in which the nodes are directly implanted in target tissue and coupled through the tissue and skin at the transmission wavelengths.

Figure 1B:
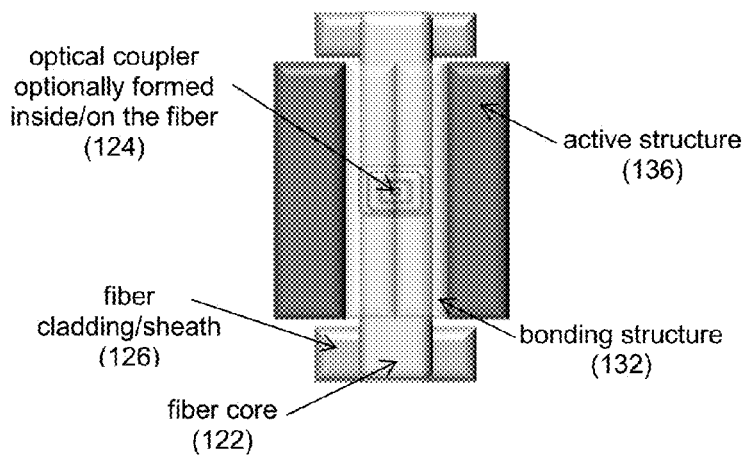

As shown in FIG. 1B, an exemplary, non-limiting coupling node includes two active structures 136 coupled optically to the fiber core 122 of the connector. Alternatively, coupling can occur by way of the fiber cladding 126.

To facilitate an optical connection between the active structure and the connector, a portion of the fiber cladding or sheath 126 can be removed to access the fiber core 122. In addition, an optical coupler 124 can be formed either within the connector (e.g., within the fiber or fiber core) or on a surface of the connector (e.g., on a surface of the fiber or fiber core).

Furthermore, a bonding structure 132 can be provided between the connector and the active structure. The bonding structure can be any useful bonding material that is optically transparent and/or facilitates an optical connection. Exemplary bonding materials include an optical adhesive, an optical tape, a polymer (e.g., a urethane polymer, a silicone polymer, or an acrylic polymer), etc., as well as any other useful material described herein.

In certain embodiments, the bonding material can be employed not only for the bonding structure but also to attach two or more active structures to each other. As shown in FIG. 1B, the bonding structure 132 attaches two active structures 136 to each other and to the optical fiber. In one embodiment, the bonding material can be employed to attach support structures (e.g., any described herein, such as a capture structure 437 in FIG. 4A). In yet another embodiment, the bonding material can be used to create a hermetic seal surrounding the active structure(s) and/or coupling nodes.

Each node can include any number of active structures, e.g., 1, 2, 3, 4, 5, or more, with any useful geometry. In at least some embodiment, a node will consist of a cluster of two, three, four, or more active structures that encircle the optical connector and may be locked into place after final assembly by a coating, such as a coating of a biologically inert polymer or any useful sealant material, e.g., any described herein. For such an arrangement, the individual active structures may include mechanical features for fiber alignment and capture (e.g., one or more capture structures), and the assembly may include one or more bonding structures (e.g., adhesive layers) for bonding the active structures to the fiber and/or to each other.

Figure 1C:
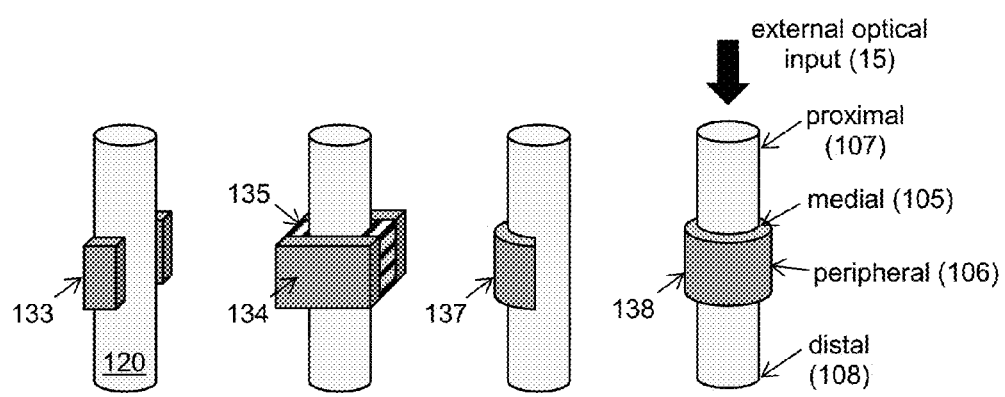

Non-limiting embodiments of various node geometries are provided in FIG. 1C. The coupling node can include a pair of rectangular active structures 133 disposed on a portion of the optical fiber 120 having a distal end 108 and a proximal end 107 for transmitting an external optical input 15, a pair of active structures 134 including a bonding structure 135, a half-ring active structure 137, and a ring active structure 138. Each coupling node includes a medial surface 105 facing the optical connector and a peripheral surface 106 facing outward to the target region.

The node can be of any useful size. For example and without limitation, the outer envelope of an individual node may be as small as 10 μm×10 μm×2 μm, or even somewhat smaller. One factor that limits the extent to which a node can be minimized is the need for optical coupling, which becomes less efficient for extremely small apertures (e.g., where the aperture is defined as the area of the active surface configured to communicate optically with the connector and/or collector).

Figure 8:
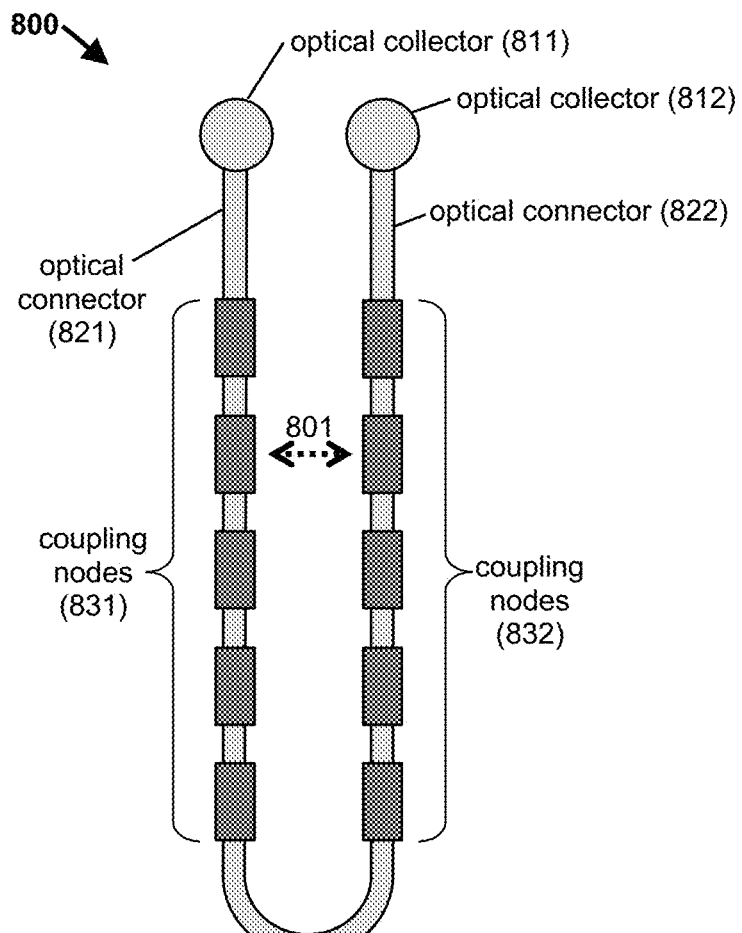
FIG. 8 shows an exemplary apparatus 800 with an alternative configuration of two optical connectors 821, 822, each including a subset 831, 832 of coupling nodes.

In addition, each active structure can communicate electrically and/or optically with any other active structure (e.g., within the same coupling node or between different coupling nodes). It should also be understood that in addition to communicating with the external unit (e.g., any herein), each node may communicate with other nodes. Although such communication will generally be most efficient if done through the optical fiber, direct transmission of inter-nodal optical and/or electrical signals through the biological medium may also be possible. For example, the connector(s) can be configured to facilitate inter-nodal communication. In one embodiment, the apparatus includes two connectors 821, 822 configured to facilitate inter-nodal communication 801 between two nodes in separate subsets 831, 832 (see FIG. 8).

Each coupling node can be hermetically sealed. Such a seal can be useful to avoid inflammation and biotoxicity at the site of implantation of the apparatus or active structure of the invention. In addition, the seal can prolong implantation time by protecting various structures and components from degradation by the cellular environment. Exemplary sealant materials for the hermetic seal, by way of example and not limitation, are polyimide, polytetrafluoroethylene, glass, a biocompatible polymer, and silicone, as well as any sealant material described herein. If there is a need for external electrodes, some appropriate conductive materials, by way of example and not limitation, are platinum, iridium oxide, tungsten, iridium, gold, titanium, and niobium.

Figure 1D:
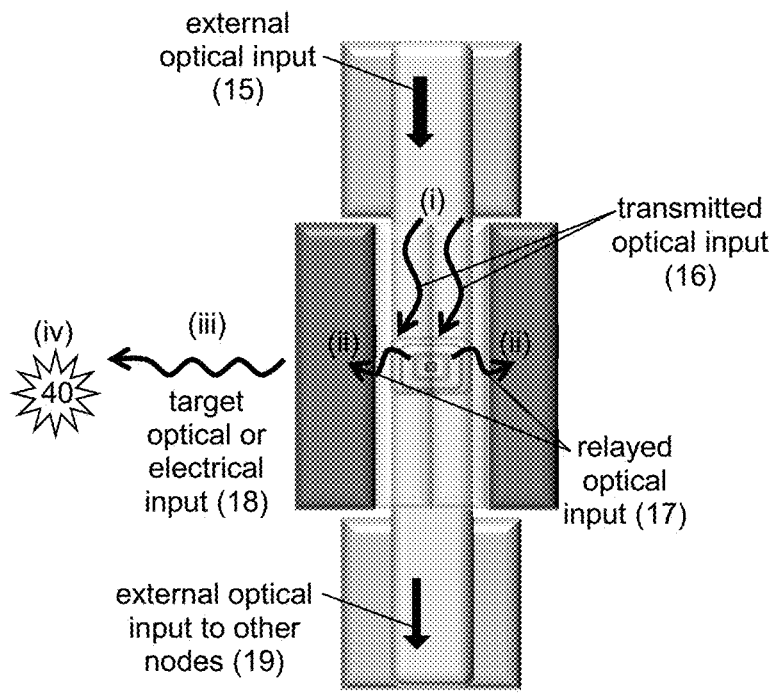

In use, the coupling node captures and directs signals to and from the target. As shown in FIG. 1D, (i) an external optical input 15 is provided to the coupling node, which results in a transmitted optical input 16 to the optical coupler. Then, (ii) the input is delivered as a relayed optical input 17 to the active structure. Next, (iii) the relayed input 17 is processed by the active structure to provide a signal (e.g., a target optical or electrical input 18) to the target 40, thereby (iv) activating or stimulating the target 40. If multiple nodes are present on the connector, then a portion of the external input is provided to other nodes 19. If the coupling nodes are injected without the optical connector, then the external optical input 15 can be delivered directly to the active structure(s).

Figure 1E:
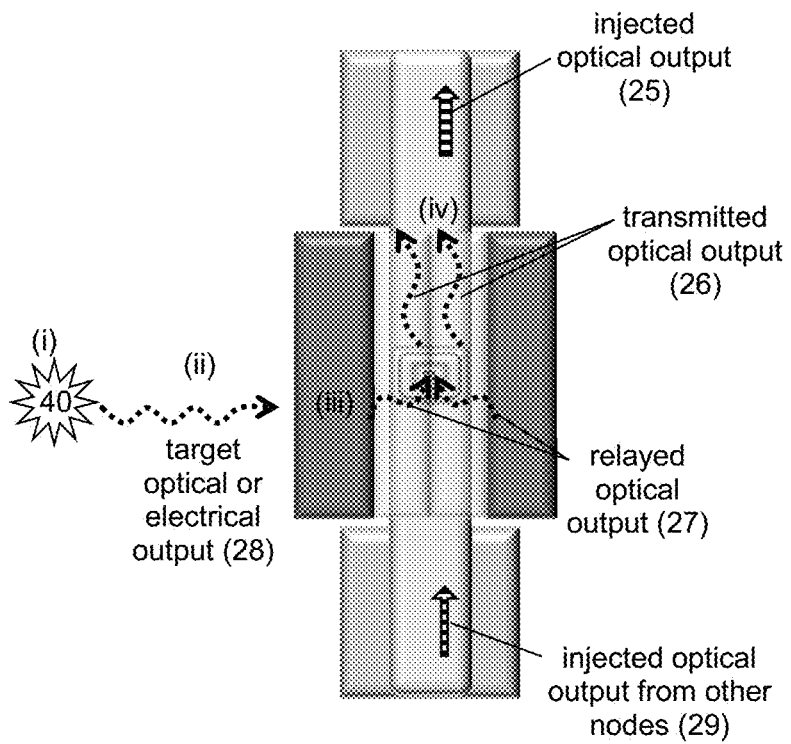

FIG. 1E provides the pathway for signals from the target 40. As can be seen, (i) the target 40 in proximity to the apparatus emits a signal, where (ii) this signal is transmitted as a target optical and/or electrical output 28 to the active structure(s). Then, (iii) this output is processed by the active structure(s), which provides a relayed optical output 27 to the optical coupler. Next, (iv) the output is transmitted from the coupler and through the optical connector as a transmitted optical output 26. If multiple nodes are present on the connector, then a portion of the injected optical output from other nodes 29 is combined to provide an injected optical output 25 to the external unit. In this manner, optical signals between an external unit and the biological target are linked by an optoelectronic structure, apparatus, or system.

In one embodiment, the active structure is a hybrid optoelectronic device in which electronic features are principally fabricated on a silicon or SOI substrate, and optical features such as diode lasers and photodiode detectors are fabricated using III-V technology and integrated with the silicon-based devices. Such devices will typically include the elements of optical transceivers for receiving data transmitted down the optical fiber, and for coupling data into the optical fiber for transmitting back to the external unit. Such devices will typically also include power photodiodes for receiving power that is optically transmitted down the fiber by the external unit, and circuitry to receive electrical output from the power diodes and condition it for use by the other integrated circuit elements. The nodes may further include storage elements, such as capacitors, for accumulating energy output by the power photodiodes over relatively long intervals and releasing it in pulses as required.

Apparatus and Methods of Fabrication

The apparatuses and systems of the invention generally include one or more coupling nodes, an optical connector, and an optical collector. The apparatus can include an array of nodes or active structures. Such arrays can be disposed on a surface of the connector or connected optically to an external input signal by way of the connector (e.g., connected to an optical fiber core of an optical fiber connector).

Figure 2A:
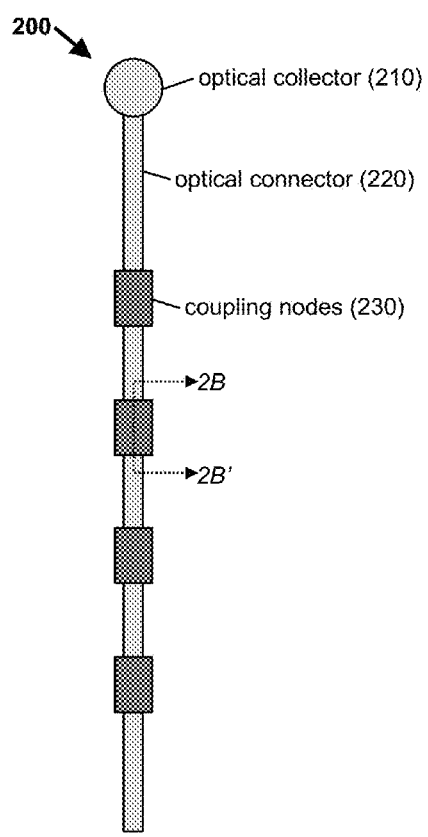
FIG. 2A-2C provides schematics of an exemplary apparatus 200 having an optical coupler 224 within the core 222 as (A) a side view, (B) a cross-sectional view along line 2B-2B', and (C) a cross-sectional view along line 2C-2C'.
Figure 2B:
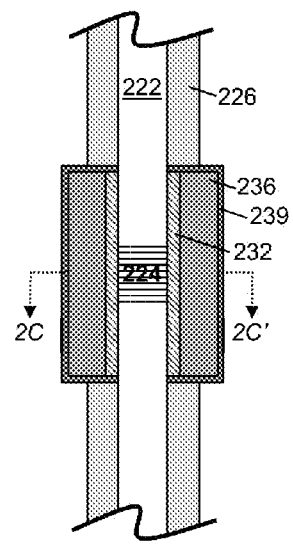
Figure 2C:
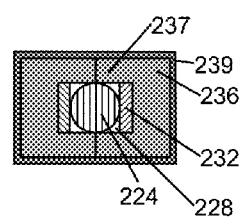

FIG. 2A-2C provides an exemplary apparatus 200 having an optical connector 220. An optical collector 210 is disposed on the proximal end of the connector, and a plurality of coupling nodes 230 is disposed generally on the distal end of the connector. As seen in FIG. 2B, each coupling node 230 includes two active structures 236. The interface between the active structures 236 and the optical fiber core 222 includes a bonding structure 232, which facilitates an optical connection between the fiber and the node. As can be seen, the cladding 226 can be removed to expose the core 222.

In the particular embodiment of FIG. 2B-2C, an optical coupler 224 is present within the core 222. The optical coupler can include a Bragg grating, an optical scattering structure, or an optical tap (e.g., any described herein). For example, nodes along the optical fiber are assembled around internal scattering structures (for example, Bragg diffractors) that couple a portion of the light into the node and pass the remaining amount to the other nodes. The region 228 disposed between the coupler 224 and the bonding structure 232, if present, can include one or more optical adhesives or polymers (e.g., any described herein).

To ensure a secure connection between the active structure and the connector, one or more fiber capture structures can be included. For instance, as seen in FIG. 2C, the active structure can include projections 237 as capture structures. These capture structures are disposed on the medial surface of the active structure and are configured to define a recess into which the optical connector can be inserted. The capture structures can include one or more optical adhesives or polymers to further promote attachment between active structures and/or between the active structure and the optical connector.

Each node or active structure(s) forming the node can include a coating 239 (e.g., a hermetic coating or seal). The coating can be formed from any useful sealant material, such as a dielectric (e.g., silicon oxide, silicon nitride, or alumina), a polymer (e.g., polydimethylsiloxane, polytetrafluoroethylene, or parylene), or any described herein.

Figure 3A:
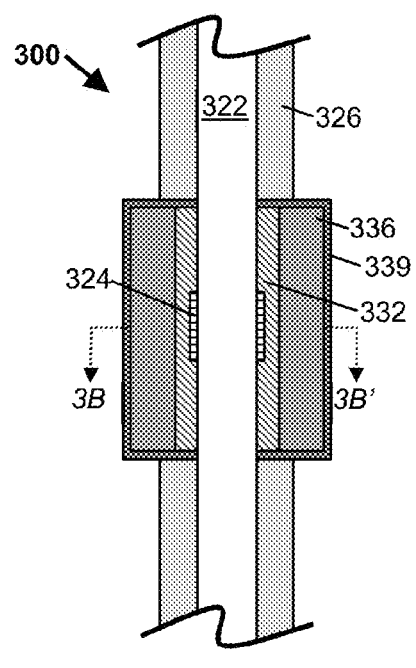
FIG. 3A-3B provides schematics of another exemplary apparatus 300 having an optical coupler 324 surrounding the core 322 as (A) a cross-sectional view of the coupling node and (B) a cross-sectional view along line 3B-3B'.
Figure 3B:
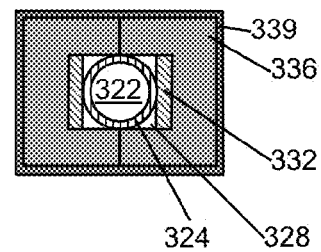

FIG. 3A-3B provides an exemplary apparatus 300 having an alternative configuration for the optical coupler 324. Here, the optical coupler 324 is disposed on a surface of the optical core 322 and beneath the cladding 326. Similar to FIG. 2A-2C, this apparatus 300 includes a coupling node, which in turn has two active structures 336 having a bonding structure 332 and a coating 339. The region 328 disposed between the coupler 324 and the bonding structure 332, if present, can include one or more optical adhesives or polymers (e.g., any described herein).

Figure 4A:
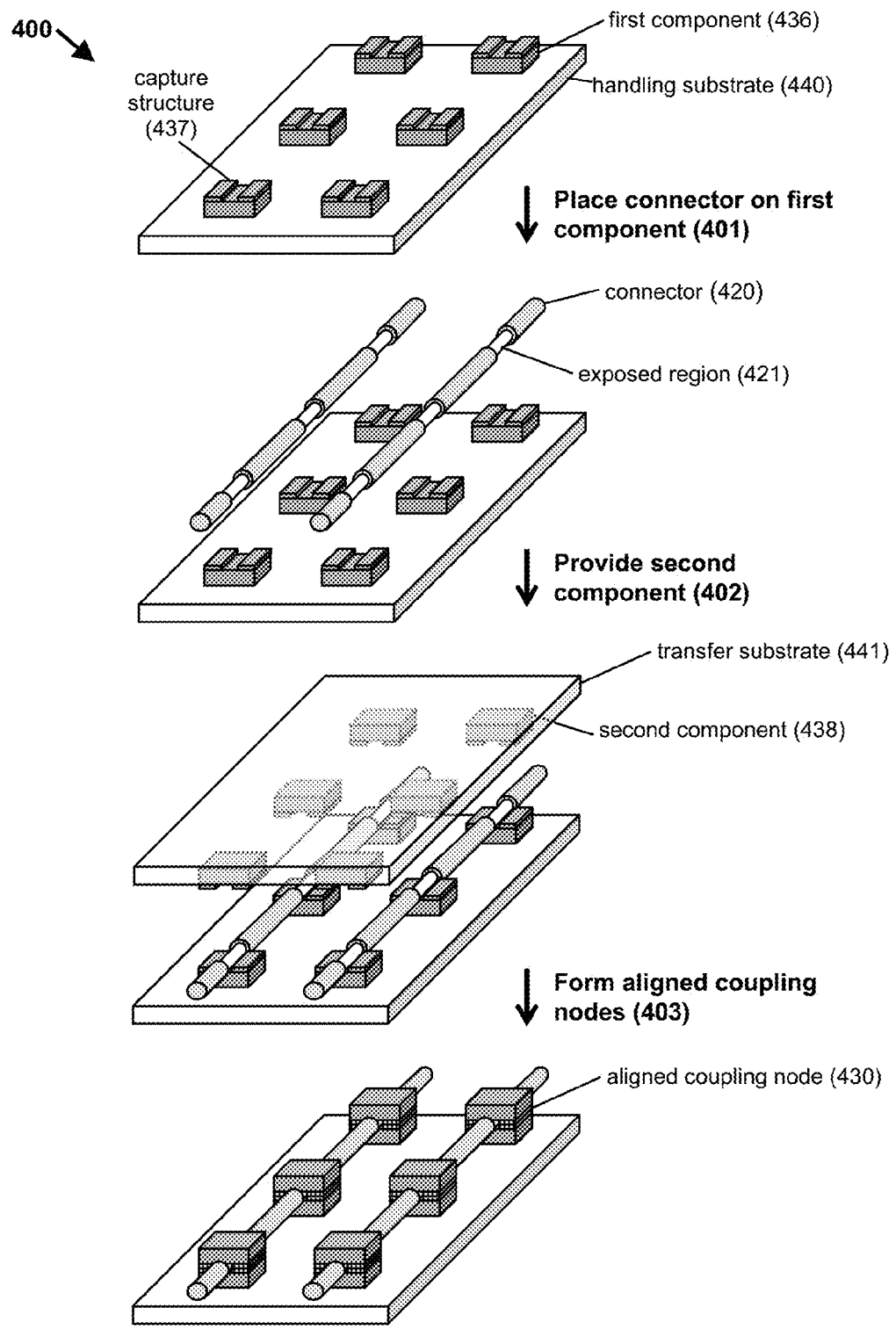
FIG. 4A-4E provides schematics of exemplary methods of making an apparatus. Provided is (A) an exemplary method 400 for aligning coupling nodes. Also provided are exemplary steps for providing a bonding structure between the core and active device(s), where exemplary steps include, independently, (B) depositing a bonding structure 4032 prior to aligning the connector, (C) providing a connector having coated regions 4132 having a bonding material, (D) depositing a bonding structure 4232 after aligning the connector, or (E) sealing the coupling node with a bonding material to provide a sealed node 4330.

The apparatus can be fabricated by any useful method. FIG. 4A provides an exemplary method 400 for aligning coupling nodes in an apparatus. In general, the method includes placing one or more connectors on one or more first components 401, providing one or more second components 402, and forming aligned coupling nodes 403, where each coupling node includes a first component and a second component. The first component 436 generally includes an active structure having one or more fiber capture structures 437.

As can be seen at the top of FIG. 4A, the method includes providing a handling substrate 440 including an array of first components 436, where each first component includes one or more fiber capture structures 437. Then, one or more connectors 420 are placed on the first components. The connectors 420 can optionally include one or more exposed regions 421, where each exposed region is configured to contact at least one first component. Next, an array of second components 438 can be provided on a transfer substrate 441. The arrangement of these second components can be configured to allow alignment of each second component with a first component. Finally, the first and second components are aligned, thereby forming aligned coupling nodes 430. Although these steps include an array of first and second components to form a plurality of apparatuses, a skilled artisan would understand that this method could be modified to form a single apparatus or any other useful n×m array (e.g., where each n and m, independently, is an integer of 1, 2, 3, 4, 5, or more).

Figure 4B:
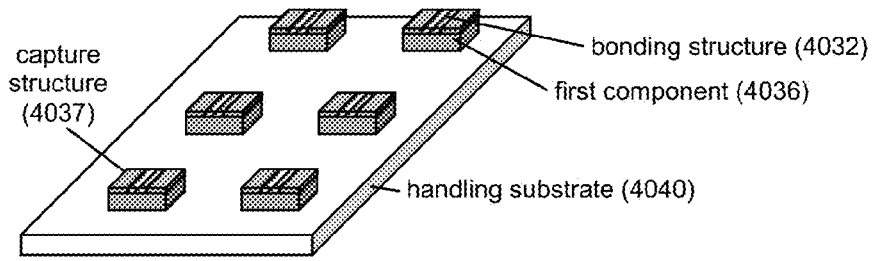
Figure 4C:
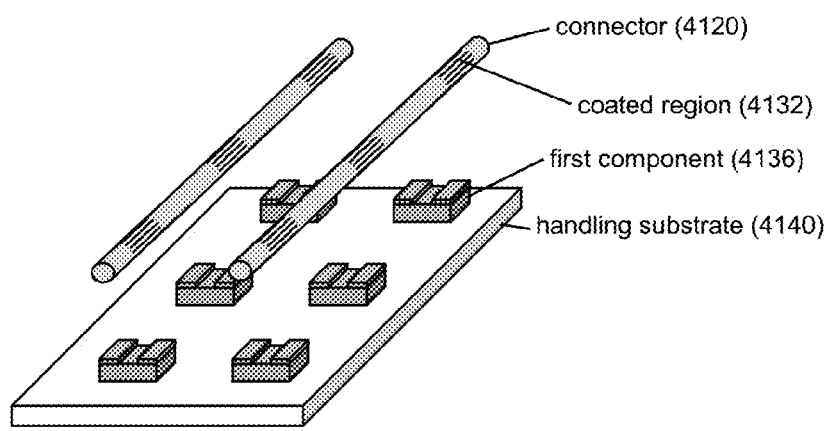
Figure 4D:
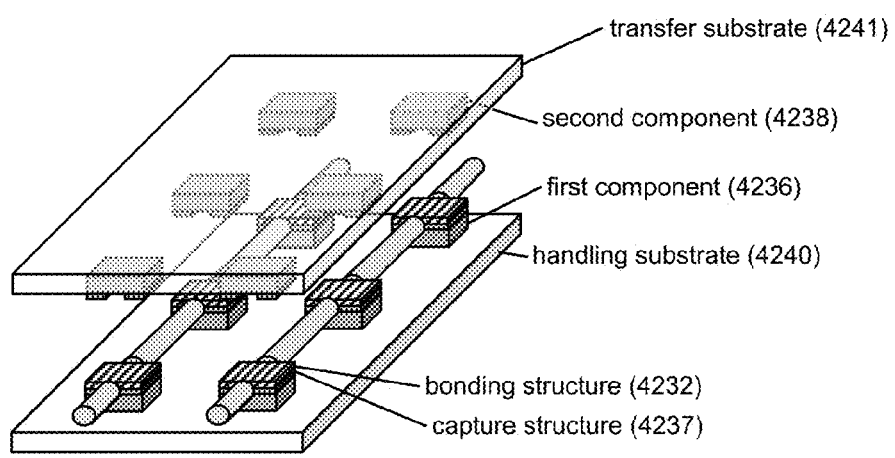
Figure 4E:
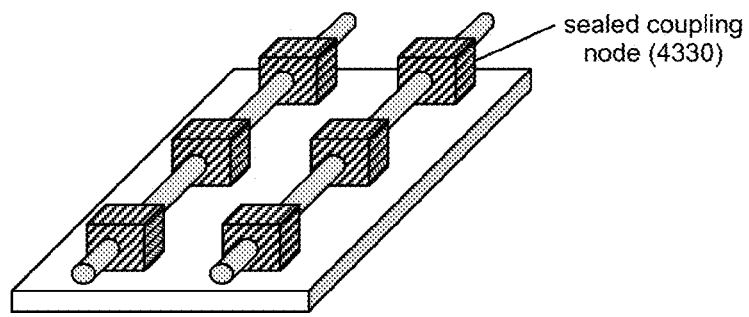

One or more bonding structures (e.g., between the connector and the active structure and/or between two active structures) can be present to provide a secure mechanical and/or optical connection between one or more elements of the apparatus. Exemplary bonding structures and steps for forming such structures are provided in FIG. 4B-4E. For example, in FIG. 4B, the bonding structure 4032 can be disposed on a surface of the first component 4036 (e.g., within a recess or on a surface of an active structure disposed between two capture structures 4037), which in turn is provided on a handling substrate 4040. In some embodiments, the bonding structure is a curable polymer, thereby allowing time to align one or more connectors with the first components.

In another example (FIG. 4C), the bonding structure is provided as a coated region 4132 on a connector 4120. With this configuration, regions of the cladding can be removed to expose the fiber core, and then these exposed regions can be treated or coated with a bonding material (e.g., an optical adhesive). Then, the coated region 4132 is aligned with the active structure of the first components 4136 on the handling substrate 4140.

In yet another example (FIG. 4D), the bonding structure 4232 can be disposed on the connector after being aligned with the first component 4236 on the handling substrate 4240. Furthermore, the bonding structure or material can be provided on one or more capture structures 4237, first components 4236, and/or second components 4238. After dispensing the bonding material, the transfer substrate 4241 having the second components 4238 is aligned with the handling substrate 4240 having the first components 4236.

In another example (FIG. 4E), the bonding structure can be disposed on a surface of the active structures after assembly with the connector. As can be seen, the bonding structure can then provide a sealed coupling node 4330. Such a bonding structure can be formed by any useful method, such as dip coating, spraying, spin coating, etc.

Any of the bonding structures herein can be formed of a useful bonding material, such as a sealant material, an adhesive, a dielectric (e.g., any described herein, such as silicon oxide, silicon nitride, or alumina), or a polymer (e.g., any described herein), in any useful form (e.g., such as a layer). In particular embodiments, the bonding structure (e.g., formed from a polymer) is overlaid on a capture structure (e.g., formed from a dielectric material, such as silicon oxide, silicon nitride, or alumina) to form a stack. The apparatus may include any other optional components (e.g., functional layers), which can be formed during the assembly process.

Biological Probe Structure (Active Structure)

The biological probe structure of the invention is an active structure. The active structure generally includes one or more detectors (e.g., photodetectors and/or electronic detectors), one or more emitters (e.g., photoemitters, electrodes, and/or electronic emitters), and circuitry (e.g., a signal processing circuitry). Optionally, one or more active structures form a self-contained or hermetically sealed unit.

The active structure can be hermetically sealed during the fabrication process. Sealing of the active structures may take place in two steps. First, the individual active structures may be encapsulated with a transparent dielectric substance, such as silicon oxide, silicon nitride, or alumina. Then, after final assembly, the nodes may be encapsulated with a polymer coating such as poly(dimethylsiloxane) (PDMS) or, via an appropriate low-temperature process, with a coating of, e.g., silicon oxide, silicon nitride, or parylene.

Exemplary active structures are provided in FIG. 5A-5E. As can be seen, one or more active structures 536 can be combined with optional bonding structure(s) 532 to form a coupling node with a fiber 520.

Figure 5A:
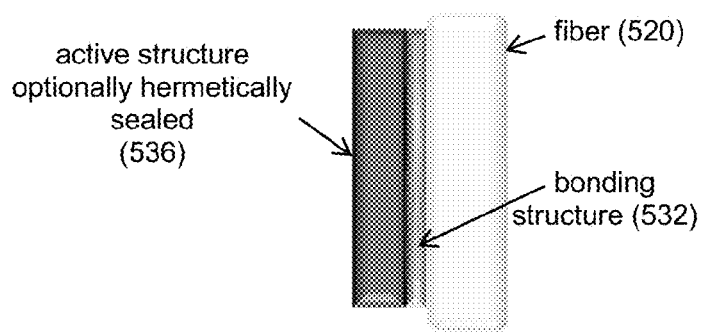
FIG. 5A-5E provides schematics of a coupling node including an active structure 536 and a bonding structure 532. Provided are (A) a side view, (B) a cross-sectional view, (C) a plan view of the medial side of the node coupled to the fiber, and (D) a plan view of the peripheral side of the node facing outward toward the biological medium. Also provided is (E) a cross-sectional view of an active device with exemplary receivers and emitters to receive and transmit optical and electrical signals.

FIG. 5A shows one active structure 536 in which the peripheral 506 surface (or the front portion) faces outward toward the biological medium, and in which a medial 505 surface (or the back portion) faces and is coupled to the optical fiber 520. In one embodiment, the medial 505 surface advantageously includes mechanical features (e.g., capture structures) for capturing the fiber and facilitating the optical coupling thereto, and will typically also include a bonding structure 532 or bonding layer 533 of an appropriate adhesive material.

The active structure can include one or more emitters, detectors, and/or receivers (e.g., any described herein) disposed on the substrate. Further, the substrate can include one or more Si cells, control electronics, and/or signal processing circuitry. In one embodiment, one or more emitters and/or detectors (e.g., configured to emit signals to and detect signals from a target) are provided on a peripheral surface of the active structure. In another embodiment, one or more receivers (e.g., configured to couple optical signals back into the optical connector) are disposed on a medial surface of the active structure. In yet another embodiment, one or more optical or electronic features (e.g., configured to extract, collect, and/or focus optical and electrical signals) are present on the peripheral surface.

Figure 5B:
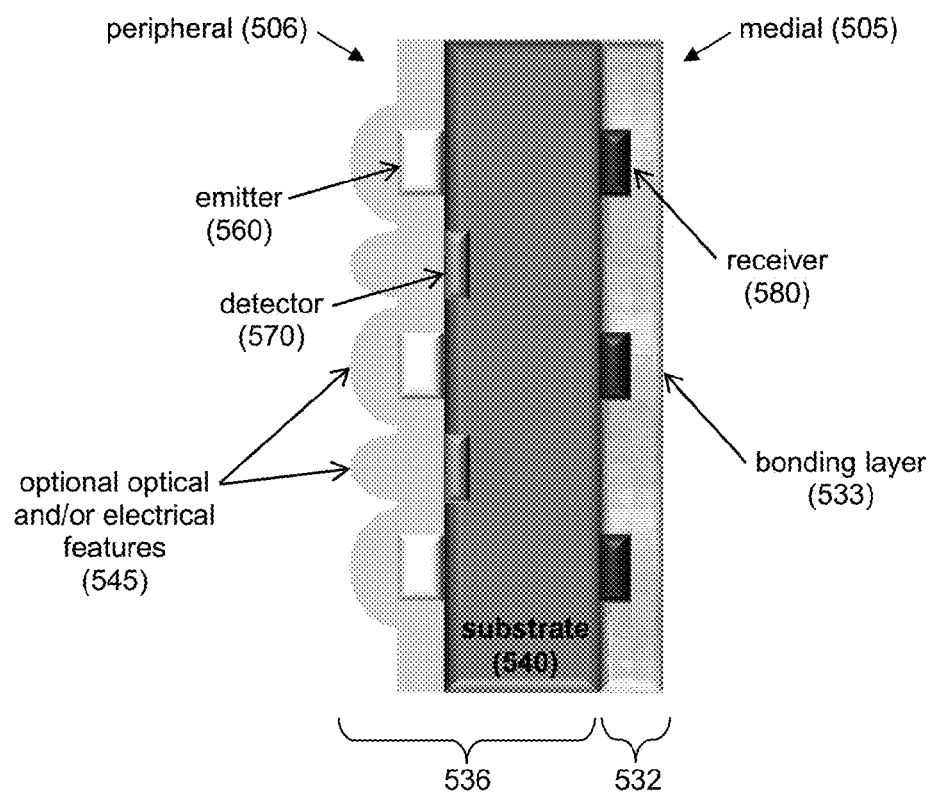

FIG. 5B provides an exemplary active structure 536 having a bonding structure 532 disposed on the medial 505 surface. The active structure 536 includes a substrate 540 having signal processing circuitry and/or control electronics. Disposed on the peripheral 506 surface of the substrate 540 are emitters 560, detectors 570, and optional optical or electrical features 545. Disposed on the medial 505 surface are receivers 580 and a bonding layer 533.

Figure 5C:
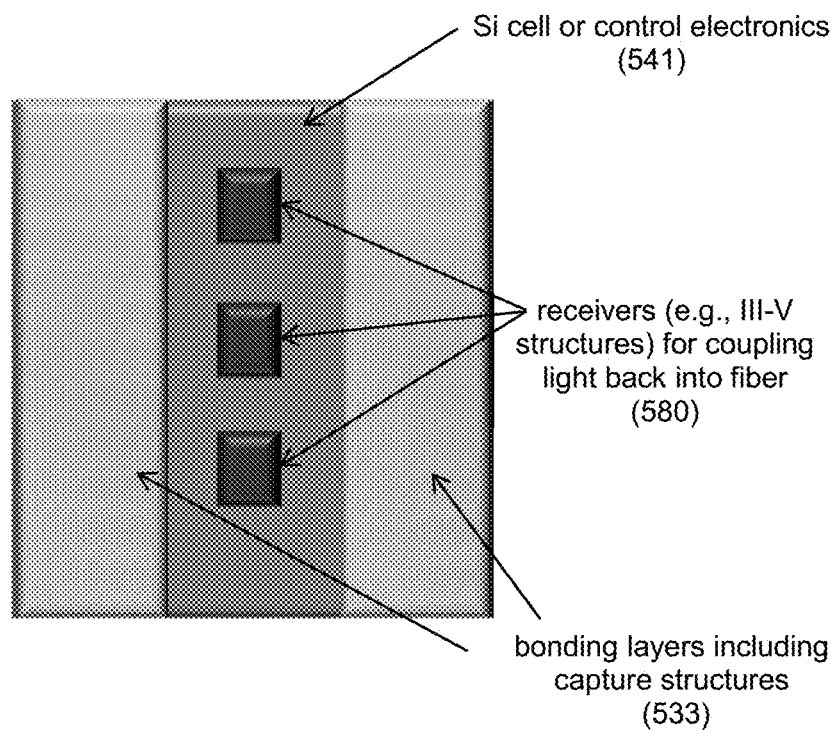

FIG. 5C provides a partially schematic plan view of the medial 505 surface of an exemplary active structure 536. As can be seen, capture structures 533 on the left and right sides project toward the view out of the plane of the figure, so as to define a slot or recess between them in which the connector is nested. The capture structures may be fabricated, e.g., from silicon oxide, silicon nitride, or a suitable polymer. Within the recess, one or more receivers 580 can be present to couple optical signals back into the fiber. In addition, the receivers 580 (e.g., an array of optoelectronic devices, exemplarily III-V devices) can be connected electronically to the silicon or III-V cell, circuitry, or control electronics 541 present on or within the substrate (e.g., silicon or silicon-on-insulator (SOI) substrate). In particular embodiments, underlying the receivers is a silicon or SOI substrate bearing electronic circuitry for power conditioning, data processing, and control.

Figure 5D:
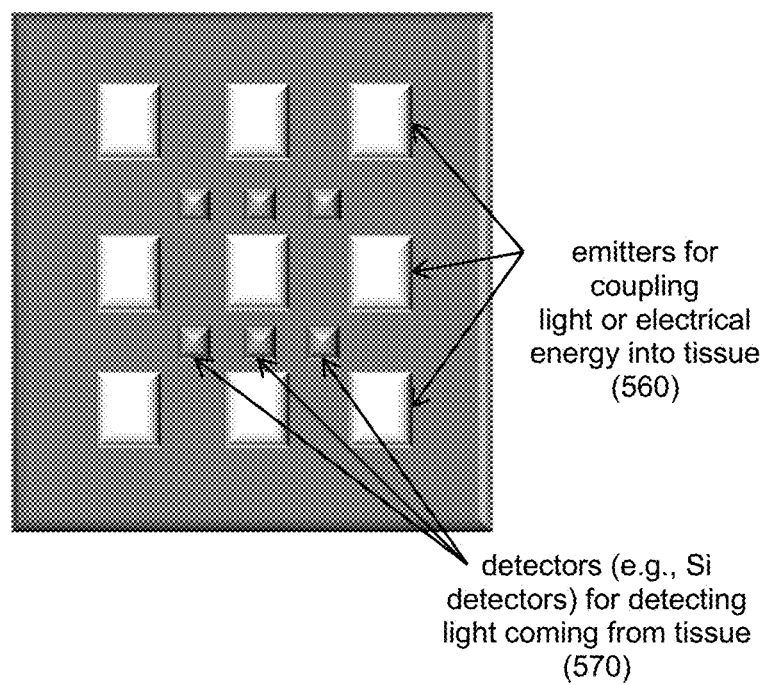

FIG. 5D provides a partially schematic plan view of the peripheral 506 surface of the exemplary active structure 536. As can be seen, there is an array of detectors 570 (e.g., silicon detectors), shown as set into the face of the substrate, for detecting light coming from biological tissue. There is also shown an array of emitters 560 (e.g., III-V optical devices and/or electrodes), shown as projecting from the substrate surface, for emitting optical and/or electrical signals into the tissue.

The peripheral 506 surface can also include one or more optical or electrical features. For instance, the optical feature can be a layer of transparent material (e.g., a polymer, such as PDMS, polycarbonate, glass, silica, etc.) that embeds the projecting portions of the optical emitters and has a lens-like conformation for facilitating the optical coupling between the emitters and the receivers and the biological medium. Exemplary optical features include a microlens (e.g., formed by a transparent polymer, such as PDMS), including those structures described in Cruz-Campa J L et al., "Microlens rapid prototyping technique with capability for wide variation in lens diameter and focal length," *Microelectron. Eng.* 2010 November; 87(11):2376-81 and Jared B H et al., "Micro-concentrators for a microsystems-enabled photovoltaic system," *Opt. Express* 2014 March 10; 22 Suppl 2:A521-7, each of which is incorporated herein by reference in its entirety.

As further seen in FIG. 5D, the emitters 560 for coupling signal(s) into the target form a two-dimensional array, as do the detectors 570 for detecting signal(s) coming from the target. The respective emitters may be conformed for photoemission at different wavelengths, depending on the photosensitivities that they are meant to exploit and the effects that are desired, or for electric signal transmission, depending on the desired current, voltage, or signal. In particular, for transmitting electrical signals, each emitter can be independently configured to act as a source or a sink, thereby controlling the direction and location of the electrical signals.

Figure 5E:
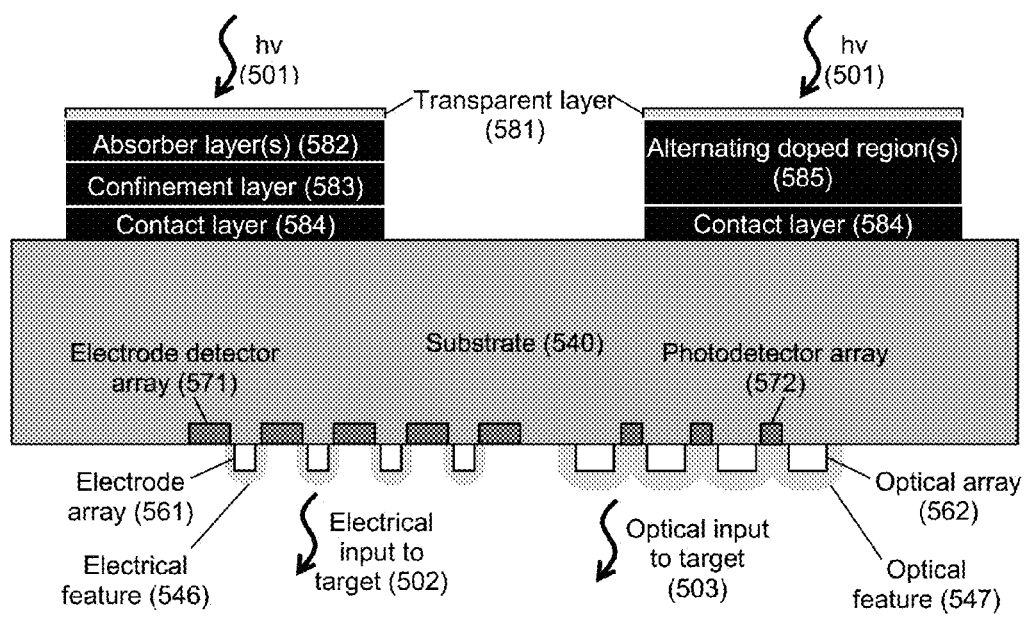

Any useful combination of receivers, detectors, and emitters can be included in the active structure. For instance, receivers are generally configured to couple light between the active structure components and the optical connector. FIG. 5E shows an exemplary active structure having two different types of receivers configured to couple an optical signal 501 from the connector, as well as to convert the optical signal into an electric signal capable of being sensed by the substrate 540 or a component thereof.

The first type of receiver includes a transparent layer 581 (e.g., configured to transmit light), one or more absorber layers 582 (e.g., configured to absorb photons, such as an n-type semiconductor, a p-type semiconductor, or a p-n junction formed between p- and n-type semiconductors, including exemplary semiconductors gallium arsenide (GaAs), indium gallium arsenide (InGaAs), or indium gallium phosphide (InGaP) that can be optionally n- or p-doped), a confinement layer 583 (e.g., a GaInP layer), and a contact layer 584 (e.g., a GaAs layer optionally having metallized contact region(s)).

The second type of receiver includes a transparent layer 581, alternating doped regions 585 disposed in a layer (e.g., alternating n-implanted and p-implanted regions disposed in a substrate, such as alternating boron-implanted and phosphorous-implanted regions in a silicon substrate), and a contact layer 584 (e.g., a metallic contact layer). Any of these types of receivers or other useful structures can be employed to couple light from the connector to the substrate of the active structure.

FIG. 5E also shows two different types of emitters and detectors, where one type is configured to emit and detect an electrical signal and a second type is configured to emit and detect an optical signal. The first type generally includes an electronic emitter that is an electrode array 561 configured to transmit an electrical input to the target 502. Optionally, the electrode can have an electrical feature 546, such as a conductive metal or polymer capable of transmitting the electrical input and/or protecting the electrode component. To detect an electrical output from the target, the electrode array 561 can be used in conjunction with an electronic detector, such as an electrode detector array 571. The detector array 571 can be connected electrically to electronic components of the substrate 540.

The second type of emitters and detectors is configured to emit and detect an optical signal. This type includes a photoemitter optical array 562 configured to transmit an optical input to the target 503. The optical array 562 can include an optical feature 547, such as a lens configured to transmit and receive optical signals. A photodetector array 572 can used to detect an optical output from the target, where the array can be connected electrically to electronic components of the substrate 540.

The receiver, emitter, and detector can have any useful structure, such as an electrode, a photovoltaic cell, a III-V structure, or a solar cell, as well as arrays thereof, including any structure or device described in U.S. Pat. Nos. 7,127,301, 8,000,804, 8,285,394, 8,323,955, 8,329,503, 8,592,249, 8,614,395, 8,680,810, 8,728,857, and 8,729,673; and U.S. Pub. Nos. 2014/0084450 and 2014/0102520, each of which is incorporated herein by reference in its entirety.

In one embodiment, the emitter and/or detector is a photovoltaic cell including a crystalline c-Si solar cell that is point-contact, back contacted, thereby having no metal shading losses and allowing for coplanar interconnections. In yet another embodiment, the emitter and/or detector is a photovoltaic cell including III-V materials (e.g., InGaP, InGaAs, InGaAsP, and/or GaAs). Exemplary cells are described in Cruz-Campa J L et al., "Microsystems enabled photovoltaics: 14.9% efficient 14 µm thick crystalline silicon solar cell," *Sol. Energy Mater. Sol. Cells* 2011 February; 95(2):551-8; Cruz-Campa J L et al., "Back-contacted and small form factor GaAs solar cell," *Proc. 35$^{th}$ IEEE Photovoltaic Specialists Conf. (PVSC)*, held on 20-25 Jun. 2010 in Honolulu, Hi., pp. 1248-52; Nielson G N et al., "Microscale c-Si (C)PV cells for low-cost power," *Proc. 34$^{th}$ IEEE PVSC*, held on 7-12 Jun. 2009 in Philadelphia, Pa., pp. 1816-21; and Tauke-Pedretti A et al., "Resistance considerations for stacked small multi junction photovoltaic cells," *Proc. 39$^{th}$ IEEE PVSC*, held on 16-21 Jun. 2013 in Tampa, Fla., pp. 2131-5, each of which is incorporated herein by reference in its entirety.

In one embodiment, the emitter is a light-emitting diode formed from GaN stack layers including undoped, n-doped, multiple quantum well, and p-doped layers. Exemplary diodes are described in McCall J G et al., "Fabrication and application of flexible, multimodal light-emitting devices for wireless optogenetics," *Nature Protoc.* 2013; 8(12):2413-28 and Rodak L E et al., "Light emitting diode growth on curved gallium nitride surfaces," *Mater. Res. Soc. Symp. Proc.* 2011; 1288:DOI: 10.1557/op1.2011.286 (6 pp.), each of which is incorporated herein by reference in its entirety. Exemplary photodetectors includes a PIN III-V detector (e.g., an InGaAs PIN detector, such as that in Sheng Z et al., "InGaAs PIN photodetectors integrated on silicon-on-insulator waveguides," *Opt. Express* 2010 January; 18(2):1756-61, which is incorporated herein by reference in its entirety).

Electrical connections between the receiver, emitter, and detector with the substrate or circuitry can include any useful connection, such as contact pads, wires, bus lines, etc. formed from any useful material, such as a metal (e.g., chromium, gold, etc.).

It should be understood that although the nodal embodiments described above are meant to be coupled to an optical connector, other embodiments are envisaged in which one or more active structures or nodes are self-contained units that are embedded within the biological system and communicate with the external unit by direct optical transmission. In particular embodiments, the system also include one or more embedded optical collectors that are not physically connected to the self-contained units. Rather, the optical collector(s) harvest light transdermally and optically relay this light to the self-contained units.

The active structures can be fabricated with any useful process. In an exemplary process for fabricating each individual device, the electronic layer (e.g., layers including the substrate, electronic emitter(s), and/or electronic detector(s)) and the optical layer (e.g., layers including photoemitter(s), photodetector(s), and/or receivers) are each made by respective, conventional silicon-based and III-V based processes, and then the various layers are bonded together using known techniques. In at least some embodiments, an active structure will include two optical layers with an electronic layer that is, e.g., sandwiched between the optical layers. In such an embodiment, one optical layer is inward-facing (on the medial surface) for coupling to the optical connector, and the other optical layer is outward-facing (on the peripheral surface) for coupling to the biological environment.

An additional step may be added to encapsulate the individual active structure (e.g., using a sealant material, such as any described herein) prior to final assembly of the node. In the final assembly stage, using known techniques of microassembly, a plurality of active structures are clustered around an optical connector using alignment features on the connector and on the active structures. The cluster can be bonded together and then encapsulated.

In one embodiment, silicon and III-V layers are bonded together in earlier steps of the process and are processed on the silicon substrate to complete the electronic and optical components of the active structure. These active structures are then assembled together to form the nodes.

Emitters, Detectors, Receivers, and Other Components

The active structure can include any number of components to transmit, receive, relay, power, and store one or more signals (e.g., optical, electrical, and/or electromagnetic signals). For instance, the structure can include an emitter configured to emit an optical or electrical signal in order to stimulate or activate the biological target. In addition, the structure can include a detector configured to detect an optical or electrical signal released by the biological target. Finally, the structure can also include a receiver configured to receive an optical input signal (e.g., from an external unit), convert this optical signal into an electrical signal, and relay this electrical signal to circuitry within or on the substrate. The circuitry, in turn, can be connected electrically to one or more emitters and detectors. In particular embodiments, the circuitry include one or more control electronics, components, and logic processes to encode and decode an electrical signal, apply an algorithm to an electrical signal into an electrical input for emitter(s) and/or detector(s), store power, and/or transmit power. Additional details on circuitry are described herein.

With regard to electrical signals, an electronic emitter or electronic detector can include an electrode, an electrochemical sensor, a transducer, an electroactive component (e.g., a microcoil for electromagnetic stimulation), as well as arrays thereof. The electrode can have any useful configuration, such as, e.g., a disk electrode, a spherical electrode, a plate electrode, a hemispherical electrode, a microelectrode, or a nanoelectrode; and can be formed from any useful material, such as gold, indium tin oxide, carbon, titanium, platinum, etc.

Exemplary electrodes include a planar electrode, a three-dimensional electrode, a porous electrode, a post electrode, a microelectrode (e.g., having a critical dimension on the range of 1 to 1000 µm, such as a radius, width, or length from about 1 to 1000 µm), a nanoelectrode (e.g., having a critical dimension on the range of 1 to 100 nm, such as a radius, width, or length from about 1 to 100 nm), as well as arrays thereof. For instance, a three-dimensional (3D) electrode can be a three-dimensional structure having dimensions defined by interferometric lithography and/or photolithography. Such 3D electrodes can include a porous carbon substrate. Exemplary 3D porous electrodes and methods for making such electrodes are described in U.S. Pat. No. 8,349,547, which is incorporated herein by reference in its entirety. In another embodiment, the electrode is a porous electrode having a controlled pore size (e.g., a pore size less than about 1 µm or about 0.1 µm). In some embodiments, the electrode is a post electrode that is a carbon electrode (e.g., formed from a photoresist (e.g., an epoxy-based resist, such as SU-8) that has been pyrolyzed), which can be optionally modified by depositing a conductive material (e.g., a conductive polymer or a metal, such as any described herein). In yet other embodiments, the electrode is a nanoelectrode including a nanodisc, a nanoneedle, a nanoband, a nanoelectrode ensemble, a nanoelectrode array, a nanotube (e.g., a carbon nanotube), a nanopore, as well as arrays thereof. Exemplary nanoelectrodes are described in Arrigan D W M, "Nanoelectrodes, nanoelectrode arrays and their applications," *Analyst* 2004; 129:1157-65, which is incorporated herein by reference in its entirety. Other exemplary neural electrodes and related structures, e.g., microactuators, are described in U.S. Pat. Nos. 7,979,105 and 8,357,187, as well as U.S. Pub. No. 2012/0323288, as well as Anand S et al., "Electrothermal microactuators with peg drive improve performance for brain implant applications," *J. Microelectromech. Sys.* 2012 October; 21(5):1172-86; Jackson N et al., "Long-term cortical recordings with microactuated microelectrodes," *Proc. 3rd Int'l IEEE/EMBS Conf Neural Eng.*, held on 2-5 May 2007 in Kohala Coast, Hi., pp. 141-3; Jackson N et al., "Long-term neural recordings using MEMS based movable microelectrodes in the brain," *Front. Neuroeng.* 2010 Jun. 18; 3:10 (13 pp.); Jackson N et al., "Nonhermetic encapsulation materials for MEMS-based movable microelectrodes for long-term implantation in the brain," *J. Microelectromech. Syst.* 2009 January 1; 18(6): 1234-45; Muthuswamy J et al., "An array of microactuated microelectrodes for monitoring single-neuronal activity in rodents," *IEEE Trans. Biomed. Eng.* 2005 August; 52(8): 1470-7; and Muthuswamy J et al., "Implantable microtechnologies for the brain: Challenges and strategies for reliable operation," *Proc. IEEE Int'l Reliability Physics Symposium (IRPS)*, held on 10-14 Apr. 2011 in Monterey, Calif., pp. 3B.2.1-3B.2.4, each of which is incorporated herein by reference in its entirety.

Exemplary electrochemical sensors include one or more of carbon nanotubes, electrodes, field-effect transistors, etc., as well as any selected from the group consisting of an ion selective electrode, an ion sensitive field effect transistor (e.g., a n-p-n type sensor), a light addressable potentiometric sensor, an amperometric sensor (e.g., having a two-electrode configuration (including reference and working electrodes) or a three-electrode configuration (including reference, working, and auxiliary electrodes)), and/or an impedimetric sensor.

Any of these electrical emitters and detectors can be further functionalized with an electrical feature, e.g., a conductive material, such as a conductive polymer, such as any described herein, including poly(bithiophene), polyaniline, or poly(pyrrole), such as dodecylbenzenesulfonate-doped polypyrrole; a metal, such as metal nanoparticles (e.g., gold, silver, platinum, and/or palladium nanoparticles), metal microparticles, and a metal film (e.g., palladium or platinum); and/or a nanotube (e.g., a carbon nanotube).

With regard to optical signals, an optical emitter or optical detector can include a photovoltaic cell, a III-V structure (e.g., including a III-V material, such as GaAs, GaN, GaP, GaSb, InN, InP, InAs, InSb, BN, BP, Bas, AlN, AlP, AlAs, or AlSb, as well as alloys thereof, such as AlGaAs, InGaAs, InGaP, AlInAs, AlInSb, GaAsN, GaAsP, GaAsSb, AlGaN, AlGaP, InGaN, AlGaInP, or InGaAsP having any useful stoichiometry), a photodiode (e.g., a light-emitting diode), a photodetector (e.g., an Si detector, such as those including p- and n-doped regions on a silicon), and a laser (e.g., a laser diode or a vertical cavity surface-emitting laser), as well as arrays thereof. Exemplary optical emitters and detectors are described in U.S. Pat. Nos. 7,127,301, 8,000,804, 8,285,394, 8,323,955, 8,329,503, 8,592,249, 8,614,395, 8,680,810, 8,728,857, and 8,729,673; and U.S. Pub. Nos. 2012/0287420, 2013/0079615, 2014/0084450, and 2014/0102520, each of which is incorporated herein by reference in its entirety.

Interconnects between optical and electronic components or two optical components can include any useful structure. Exemplary interconnects include pillars, heterostructures, ferrules, v-grooves, flip-chip bonds, or capped structures, as well as any described in Chen R et al., "Nanolasers grown on silicon," *Nature Photon.* 2011 March; 5:170-5; Ohira K et al., "On-chip optical interconnection by using integrated III-V laser diode and photodetector with silicon waveguide," *Opt. Express* 2010 July; 18(15):15440-7; and El-Fatatry A, "Optical microsystems, mechano-optical-electro-mechanical systems—MOEMS," in *MEMS Aerospace Applications*, February 2004 (79 pp.), NATO Science and Technology Organization (Ref. No. RTO-EN-AVT-105); as well as U.S. Pat. No. 7,773,840, each of which is incorporated herein by reference in its entirety.

Other components may be present in or on the substrate, active structure, or coupling node. For instance, one or more power components (e.g., power photodiodes) can be present to provide internal electrical power to a hermetically sealed unit. In one embodiment, the component is a power photodiode for receiving power that is optically transmitted down the fiber by the external unit, and circuitry is present to receive electrical output from the power diodes and condition it for use by the other integrated circuit elements.

In another instance, one or more storage components (e.g., capacitors) can be present for accumulating energy output by the power photodiodes over relatively long intervals and releasing it in pulses as required.

Functional Layers

Any component of the active structure, coupling node, optical coupler, or optical connector can include a functional layer. Exemplary layers include optical functional layers (e.g., a light-activated material, an optically interrogatable material, a detection material, or a photoemissive material), modulation layers, ionic layers, conductive polymers, biocompatible layers (e.g., biocompatible polymers), or polymeric layers.

Optical functional layers include a light-activated material, an optically interrogatable material, a detection material, or a photoemissive material, as well as any other material capable of being addressable by light. For instance, the optical functional layer can include a membrane (e.g., formed of any useful material, such as porous aluminum oxide, acrylic copolymers, polyvinylidene fluoride, polyurethane isocyanates, polyalginate, cellulose acetate, polysulfone, polyvinyl alcohols, polyacrylonitrile, and derivatives and mixtures thereof) and a photoswitchable layer (e.g., a layer including one or more proteins that are switchable by light or a layer including one or more photoisomerizable polymers, such as any described herein). Exemplary materials for optical functional layers include photoisomerizable polymers (e.g., azobenzenes, stilbenes, spiropyrans, spirooxazines, diarylethenes, hemithioindigos, and thiophenefulgides), gels (e.g., hydrogels) including one or more photoswitches (e.g., any described herein), photoswitches (e.g., a spiropyran or an azobenzene), membranes (e.g., a polymeric membrane, a crown ether polymeric membrane, a macroporous polyethylene, etc., where each of these can include a photoswitch or photoisomerizable polymer grafted within or coated upon the membrane), as well as any described in Ercole F et al., "Photo-responsive systems and biomaterials: photochromic polymers, light-triggered self-assembly, surface modification, fluorescence modulation and beyond," *Polym. Chem.* 2010; 1:37-54 and Szymanski W et al., "Reversible photocontrol of biological systems by the incorporation of molecular photoswitches," *Chem. Rev.* 2013; 113:6114-78, each of which is incorporated herein by reference in its entirety.

Such optical functional layers can be employed as ionic layers or modulation layers. For instance, the optical functional layer can be connected fluidically to a reservoir containing any useful agent, such as an ionic species (e.g., an ion or a precursor or analog thereof, as well as any ionic species described herein), a modulator (e.g., a neurotransmitter or a precursor or analog thereof, as well as any modulator described herein), or a therapeutic agent (e.g., a dopaminergic agent, an anticholinergic agent, an agonist, an antagonist, an inhibitor, an anticonvulsant, an antiarrhythmic agent, etc.), where optical activation of the photoswitchable layer results in release of the agent. In another instance, the optical functional layer can include an agent linked by a photoisomerizable polymer or photoswitch, where activating the polymer or switch releases the agent from the layer. Exemplary linked agents include a spiropyran-modified modulator or ionic species.

Alternatively, the optical functional layer can be employed to modify, activate, and/or deactivate a target, an ionic species, a modulator, or a therapeutic agent. For instance, the optical functional layer can be a material on the surface of the nodes that is light activated and controls local concentrations of ionic species, modulators, or therapeutic agents.

In some embodiments, the apparatus or active structure includes a modulation layer. In one embodiment, the modulation layer includes a membrane and a photoswitchable layer. In yet another embodiment, the modulation layer includes a controlled release layer, which has a biocompatible material (e.g., any described herein, such as a sealant material) and a modulator disposed within the material. Controlled release includes diffusion of the modulator through the material, erosion of the material thereby causing release of embedded modulator compounds, and/or swelling of the material thereby releasing modulator compounds. Such modulation layers can be disposed on a peripheral surface of the hermetically sealed unit. The membrane can be connected fluidically to a reservoir containing one or more modulators. Exemplary modulators includes neurotransmitters (e.g., acetylcholine, aspartate, dopamine, epinephrine, gamma amino-butyric acid (GABA), glutamate, glutamine, noradrenaline, norepinephrine, and serotonin), neuropeptides (e.g. substance P, neuropeptide Y, somatostatin, VIP, neurotensin, encephalin, etc.), neuromodulators (e.g., dopamine, serotonin, acetylcholine, and histamine), and signaling molecules (e.g., ions, such as $Na^+$, $K^+$, and $Ca^{2+}$), as well as precursors, analogs, agonists, antagonists, blockers, derivatives, inhibitors, and fragments thereof (e.g., L-dopa, bromocriptine, carbidopa, bradykinin, action potential blockers, calcium channel modulators (e.g., calcium channel blockers, such as ethosuximide or nifedipine), glutamate antagonists, sodium channel modulators (e.g., sodium channel blockers, such as phenytoin or carbamazepine), potassium channel modulators (e.g., potassium channel openers, such as retigabine, or potassium channel blockers, such as a conotoxin, tetrodotoxin, or saxitoxin), an indirect GABA agent (e.g., a GABA blocker or a GABA analog, such as valproate, pregabalin, or gabapentin), a GABA receptor agonist (e.g., barbiturates and benzodiazepines, such as diazepam or lorazepam), as well as any described in U.S. Pat. Nos. 4,892,538 and 5,474,547, each of which is incorporated herein by reference in its entirety).

In some embodiments, one or more ionic layers are disposed on a peripheral surface of the hermetically sealed unit. One type of ionic layer might include a reservoir of an ionic species for controlled release, separated from the biological medium by a membrane having controllable permeability to the ionic species. Such a membrane might be made, for example, from porous aluminum oxide. The control over the permeability might be provided by a layer, e.g. a protein layer, that is switchable, upon absorption of light at an activating wavelength, between a state that blocks diffusion through the membrane and a state that permits diffusion. Alternatively, or in addition, a voltage might be applied to drive the desired ions out of the reservoir and into the surrounding medium. In yet another embodiment, the ionic layer includes a controlled release layer, which has a biocompatible material (e.g., any described herein, such as a sealant material) and an ionic species disposed within the material. Exemplary ionic species include an ion (e.g., $Na^+$, $K^+$, and $Ca^{2+}$), an ion precursor, an ion analog, a caged ion species (e.g., caged $Ca^{2+}$, such as a $Ca^{2+}$-ligand complex, where the ligand can be nitrophenyl-ethylene glycol tetraacetic acid) (NP-EGTA) or 1-(4,5-dimethoxy-2-nitrophenyl)-ethylenediaminetetraacetic acid (DM-nitrophen)), an ion channel agonist, or an ion channel modulator (e.g., a calcium channel blocker, a potassium channel blocker, or a sodium channel blocker, including any described herein).

In another embodiment, the ionic layer is configured to control local ion concentrations, which such local concentrations can be used to propagate electrical signals to nearby neuronal cells. For instance, the ionic layer can be a material on the surface of the nodes that is light activated and controls local concentrations of ionic species—this would appear as an electrical signal and couple into the nearby cells, without having to genetically modify the cells. It might also be possible to sense or detect the presence of increased ionic concentrations, to record neural activity again without having to modify the cells.

Figure 7A:
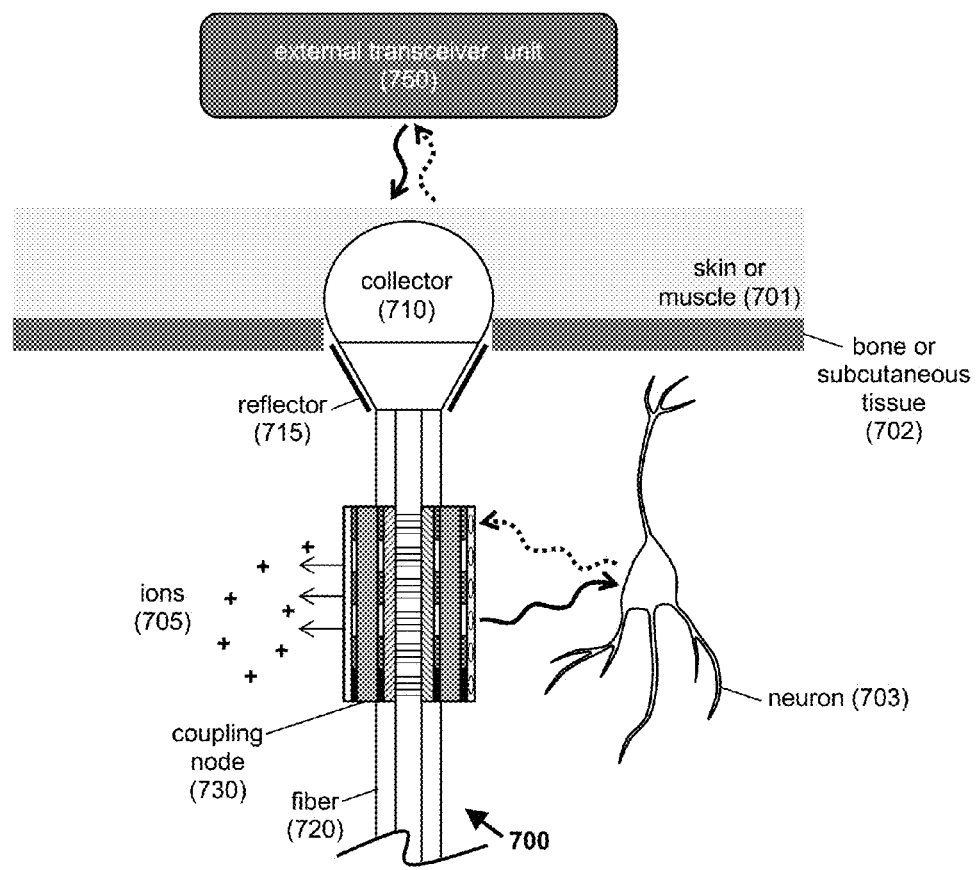
FIG. 7A-7B provides schematics of (A) an embedded apparatus 700 receiving transcutaneous optical transmissions from an external device 750 and (B) a cross-sectional view of a coupling node of the apparatus 700.
Figure 7B:
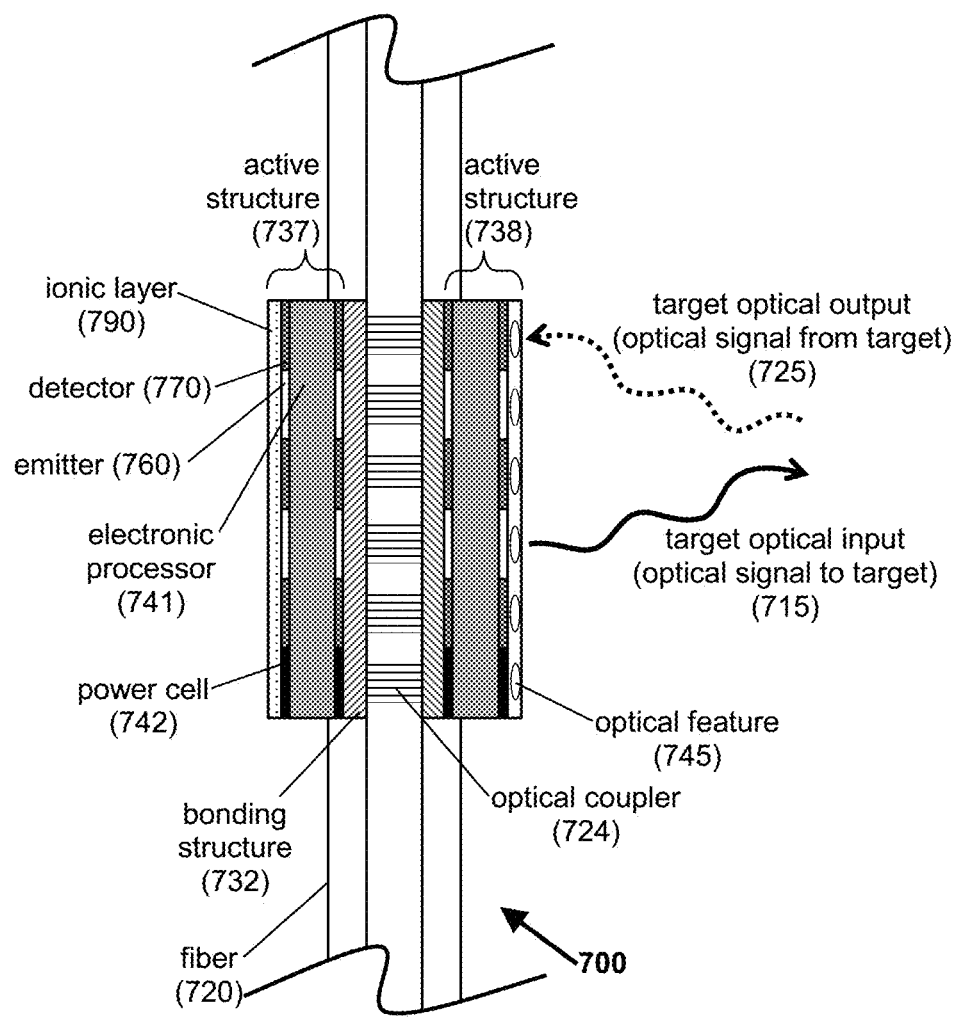

FIG. 7A-7B provides an exemplary apparatus 700 having an ionic layer 790. Shown are the embedded fiber 720 and one node 730. The collection optic 710 is shown as a modified ball lens in which the upper portion is hemispherical, and the lower portion is conical and provided with a reflective coating 715 for greater coupling efficiency. The collection optic 710 is end-fire coupled to the optical fiber 720, which includes optical couplers 724. It should be noted, however, that such a configuration for the collection optic is exemplary only and not meant to be limiting. The node 730 includes an ionic layer 790 to release one or more ions 705, as well as an active structure that transmits and receives signals from a neuron 703. The apparatus 700 is embedded within the skin or muscle layers 701, where the collector 710 is located above the bone or subcutaneous tissue 702 to facilitate optical connection to the external unit 750.

Two active nodal structures 737, 738 are shown, each having a central electronic processing layer 741 and peripheral and medial arrays of optoelectronic devices as described herein, such as detectors 770 and emitters 760 with optical features 745. Each active structure is shown as also including a power cell 742 that contains a silicon photodiode, as well as a bonding structure 732. One of the active structures is shown as optically coupling to a neuron by way of target optical output 725 and input 715 signals. The other is shown as including an external ionic layer 790 for coupling to the ionic environment surrounding the node. Such a layer may be photochemically stimulated, for example, to release calcium or other ions so as to alter the local chemical environment.

Conductive layers can be present on one or more electronic emitters or detectors (e.g., electrodes). Exemplary conductive materials for such layers include a conductive polymer (e.g., poly(bithiophene), polyaniline, or poly(pyrrole), such as dodecylbenzenesulfonate-doped polypyrrole); a metal, such as metal nanoparticles, metal microparticles, or a metal film; or a nanotube; as well as composites thereof.

Polymeric layers can be present on any useful surface, such as the surface of the active device, coupling node, connector, collector, emitter, detector, and/or receiver. Exemplary polymeric materials for such layers include an antifouling polymer, a biocompatible polymer (e.g., chitosan), a cationic polymer, etc.

Optical Connector

The optical connector connects an external optical input, which is collected by the optical collector, and relays this optical input to the coupling node and/or the active structures. Exemplary optical connectors include an optical fiber or a waveguide (e.g., a rectangular, slab, planar, or strip waveguide). Connectors can be formed from any useful material, including glass, a polymer, a silica, a photonic crystal (e.g., ID, 2D, or 3D photonic crystals), or a semiconductor; and can have any useful form, such as, e.g., a single mode or a multimode optical fiber, as well as arrays thereof. Exemplary optical connectors and materials are described in U.S. Pat. Nos. 6,445,939 and 6,564,087, as well as U.S. Pub. Nos. 2009/0326384, 2013/0030274, 2013/0039616, 2014/0024902, and 2014/0142664, each of which is incorporated herein by reference in its entirety.

FIG. 1B provides an exemplary connector that is an optical fiber. As can be seen, the optical fiber includes a core 122 and a cladding 126, which are typically of glass, and may further include a sheath 126, which is typically of polymeric composition. In the example of the figure, the sheath, and optionally some or all of the cladding, is removed in the vicinity of the node, e.g., to provide alignment and more effective optical coupling to optical emitters and/or detectors internal to the node.

The optical connector can include one or more structures to appropriately relay optical signals. For instance, as shown in FIG. 1B, the connector can include an optical coupler 124. In order for the optical connector to function effectively as a bus line delivering optical signals and/or optical power to the individual nodes, and receiving optical signals from the individual nodes for delivery to an external unit, it is desirable to include features that couple light into and out of the fiber at the nodal locations. Such a feature is indicated as an optical coupler 124. Exemplary such structures are Bragg gratings or other optical scattering structures. The optical coupler can be formed inside or on the connector.

Furthermore, when a plurality of nodes is present, then the external optical input should be apportioned as appropriate to each of the nodes. This can be achieved by using Bragg diffraction. In one embodiment, the optical connector can include an internal scattering structure or an optical tap configured to provide split an external optical input into one or more optical input signals. Each coupling node can be arrayed along the optical connector near the scattering structure or tap, such that a portion of the light incident on each scattering structure or tap is coupled into a corresponding coupling node. For instance, the optical tap can include a cladding mode structure (e.g., a bend, a misaligned fusion splice, a periodic deformation, a phase grating, etc.) integral with the optical connector, such that optical energy in the cladding modes propagates outward from the structure. Other exemplary internal scattering structures are described in U.S. Pat. No. 6,535,671 and Zhang C et al., "Broadband optical fiber tap based on cladding-mode coupling," *Opt. Eng.* 2012 July; 51(7):075001 (6 pp.), each of which is incorporated herein by reference in its entirety.

The connector(s) can have any useful configuration. For instance, the connector can include a single, elongated structure (see, e.g., FIG. 1A). In another instance, two connectors can be present to provide two subsets of nodes, where the first subset can be coupled with the second subset. An exemplary apparatus having this configuration is provided in FIG. 8. As can be seen, the apparatus 800 includes a first optical connector 821 and a second optical connector 822, where these connectors are joined by an adjoining U-shaped connecting piece. Each connector 821, 822 has an optical collector 811, 812. The first connector 821 includes a first subset of coupling nodes 831, whereas the second connector 822 includes the second subset 832. Inter-nodal communication 801 between a first node in the first subset 831 and a second node in the second subset 832 can be envisioned in this configuration. For instance, an electrical signal, e.g., current, can be applied to the tissue or targets located between the first and second nodes by having one node be a source and the other node be a sink. In another instance, an optical signal can be applied to the target located between the first and second nodes by having each node emit photons simultaneously (e.g., by employing two photon excitation). In yet another instance, a single signal can be emitted by a first node, and the second node can be configured to detect the resultant signal from the target. A skilled artisan would understand that different types of signals (e.g., optical and/or electrical signals) and different nodal configurations (e.g., configured to either receive, transmit, or relay a signal) could be implemented.

Figure 9:
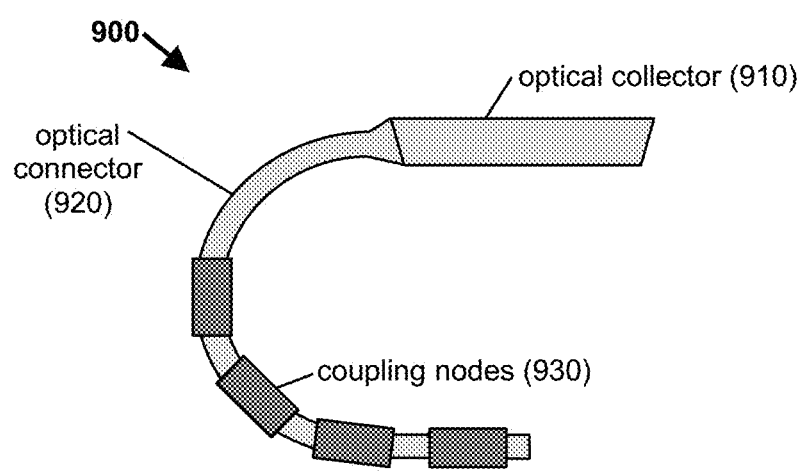
FIG. 9 shows another exemplary apparatus 900 with a planar optical collector 910.

In another configuration, the connector can have a curved geometry. As seen in FIG. 9, the apparatus 900 includes a curved connector 920 having a plurality of coupling nodes 930. In addition, the optical collector 910 includes a planar lens to provide additional surface area to harvest light. The curved configuration can be useful for accessing peripheral nerve bundles while maintaining the main plane of the collector in an orientation that is parallel to the skin surface in order to maximize light harvesting. For instance, the distal end of the curved connector can be inserted into nerve bundles or fascicles whose longitudinal axis is parallel to the skin surface. In this manner, the intra-neural longitudinal configuration of the apparatus allows for selective fascicle stimulation, as well as optimal electrode placement. In addition, the geometry and placement of the collector can be optimized for maximal light harvesting by the collector. Alternatively, the connector can be configured to allow a cuff configuration of the apparatus, where the connector can be wrapped around the nerve bundle. Other exemplary apparatus configurations includes a penetrative electrode configuration having shaft electrodes that can be inserted by pneumatic insertion techniques and a regenerative electrode having openings for nerve growth through those openings.

Optical Collector

The optical collector collects light from an external unit and relays this optical input to the coupling node(s) or active structure(s). The optical collector may be physically connected to the node(s) or structure(s) (e.g., by way of an optical connector). Alternatively, the optical collector is embedded in the target region in proximity to self-contained units that are embedded within the biological system. The optical collector can communicate with these self-contained units by direct optical transmission.

The collector can be any useful collecting optical element, such as a lens, including a ball lens, a convex lens, a dielectric lens, a planar lens, a cylinder lens, and/or a compound parabolic concentrator. The collector can include any useful components, including diffraction gratings, reflectors, and/or optical coatings.

FIG. 7A shows an exemplary collector 710 that is a ball lens. As can be seen, the apparatus 700 is placed under the skin or muscle 701 and bone or subcutaneous tissue 702. The collector 710 collects light transmitted from the external unit 750, couples it to an optical fiber 720, and transmits light back to the external unit 750 coming back on the fiber 720. Optionally, the collector 710 includes a reflector 715 to optimize optical signal transmission and reception. Nodes 730 along the optical fiber are assembled around internal scattering structures (for example, Bragg diffractors) that couple a portion of the light into the node and pass the remaining amount to the other nodes. As needed, one or more components can be employed to focus or direct optical signals, such as actuators, filters, servos, objective lenses, collimators, splitters, mirrors, reflectors, and/or optical windows, e.g., such as any described herein and in Cheng H D et al., "Monolithic bi-directional linear microactuator for light beam manipulation," *IEEE/LEOS Int'l Conf on Optical MEMS and Their Applications*, held on 21-24 Aug. 2006 in Big Sky, Mont., pp. 122-3; Chiu Y et al., "MEMS-based miniature optical pickup," *IEEE Trans. Magn.* 2005 February; 41(2):967-70; and Zhu L et al., "Fiber-coupled light-emitting diode with a capillary-bonded hemispherical lens," *IEEE Photon. Technol. Lett.* 2011 December; 23(24):1857-9, each of which is incorporated herein by reference.

Materials

Any structure herein can be formed from any useful material.

Structures that detect, transmit, or receive optical signals can be formed from any material capable of transmitting light with negligible absorption losses. Such materials include silicon (e.g., c-Si), silicon nitrides (e.g., SiON or $Si_3N_4$), silicates (e.g., germanosilicates), germanium, ZnSe, ZnS, a polymer (e.g., polydimethylglutarimide) with optional dopants (e.g., $GeO_2$), etc., in any useful form, including slab waveguides, nanowires, optical ring resonator, grating couplers, etc. Exemplary photonic materials and optical couplers are described in Cristea D et al., "Integrated optics on silicon for sensor applications," *Proc. 9th Mediterranean Electrotechnical Conf*, held on 18-20 May 1998 in Tel-Aviv, vol. 2, pp. 1444-8; Cristea D et al., "Silicon opto-FET coupled to waveguides for integrated optical microsystems," *Proc. SPIE*, held on 1998 Sep. 16 in Beijing, China, vol. 3551, pp. 63-74; Justice J et al., "Wafer-scale integration of group III-V lasers on silicon using transfer printing of epitaxial layers," *Nature Photon.* 2012 September; 6:610-4; Draper B et al., "Radiation response of a gate-all-around silicon nano-wire transistor," *IEEE Trans. Nucl. Sci.* 2009 November; 56(6):3274-9; Hall N A et al., "Surface and bulk-silicon-micromachined optical displacement sensor fabricated with the SwIFT-Lite™ process," *J. Microelectromech. Sys.* 2006 August; 15(4):770-6; Muller R et al., "3D microstructures integrated with optical waveguides and photodiodes on silicon," *Proc. 9th Mediterranean Electrotechnical Conf.*, held on 18-20 May 1998 in Tel-Aviv, vol. 1, pp. 392-5; Natarajan C M et al., "Superconducting nanowire single-photon detectors: physics and applications," *Supercond. Sci. Technol.* 2012; 25:063001 (16 pp.); Shi W et al., "Silicon photonic Bragg-grating couplers for optical communications," *Proc. SPIE* 2014 February; 9010: 90100F (12 pp.); Sparks J R et al., "Templated chemically deposited semiconductor optical fiber materials," *Annu. Rev. Mater. Res.* 2013; 43:527-57; Vahala K J, "Optical microcavities," *Nature* 2003 August; 424:839-46; Van Thourhout D et al., "Nanophotonic devices for optical interconnect," *IEEE J. Sel. Top. Quantum Electron.* 2010 September/October; 16(5):1363-75; and Ziaei-Moayyed M et al., "Gate-all-around single-crystalline silicon nanowire optical sensor," *Proc. 16th Int'l Solid-State Sens. Actuat. Microsys. Conf.* (*TRANSDUCERS*), held on 5-9 Jun. 2011 in Beijing, China, pp. 1757-60; as well as U.S. Pub. No. 2013/0085398, each of which is incorporated herein by reference in its entirety.

To further minimize optical coupling loss between the connector and the receiver(s), the medial surface of the active structure may be patterned with windows in an opaque material (e.g., aluminum) with an optional anti-reflection coating. In use, an optical signal would be transmitted through the window but not the surrounding opaque material, thereby minimizing losses due to structural misalignment and mismatches in cross-sectional areas and numerical aperture. Such windows may be present between any structures in which an optical signal is being transmitted (e.g., between the photodetector and the substrate, the collector and the connector, and/or the connector and the receiver).

Structures may also be treated with a sealant material to form a hermetic seal, thereby protecting optoelectronic components from the environment. Such structures may include the surface (e.g., the peripheral surface) of the active structure(s), coupling node(s), detector(s), emitter(s), collector(s), and/or connector(s). Exemplary sealant materials include poly(imide), benzocyclobutene, glass, a biocompatible polymer (e.g., poly(lactic acid) (PLA) including poly (DL-lactic acid) (DL-PLA), poly(L-lactic acid) (L-PLA), and poly(D-lactic acid) (D-PLA); poly(glycolic acid) (PGA); poly(lactic-co-glycolic acid) (PLGA) including poly (DL-lactic-co-glycolic acid) (DL-PLGA); a poly(ester), such as polyhydroxybutyrate, polyhydroxyvalerate, or copolymers thereof; poly(vinyl alcohol); poly(dioxanone); poly (caprolactone); poly(orthoester); poly(anhydride); poly (phosphazine); poly(propylene carbonate); poly(propylene succinate); poly(urethane); as well as copolymers thereof), a liquid crystal polymer (e.g., Vectra®NT 1300, available from Celanese Corp., Irving, Tex.), a dielectric (e.g., silicon dioxide or an epoxy polymer), a fluoropolymer (e.g., a fluoroacrylate or polytetrafluoroethylene), a photoresist (e.g., AZ® 3312 photoresist (18 cps) including a mixture of 1-methoxy-2-propanol acetate, diazonaphthoquinonesulfonic ester, and ethyl lactate, available from AZ Electronic Materials USA Corp., Branchburg, N.J., or SU-8 including an epoxy based monomer, gamma butyrolactone, propylene carbonate, and antimony salts (triarylsulfonium/hexafluoro-antimonate salt), available from MicroChem, Newton, Mass.), and silicone (e.g., a silicone gel, such as Dow Corning® 3-4680, or PDMS), as well as any described in Hassler C et al., "Polymers for neural implants," *J. Polym. Sci. B Polym. Phys.* 2011; 49:18-33, which is incorporated herein by reference.

Electrical components can include any useful metallization and passivation materials, such as a metal (e.g., platinum, tungsten, iridium, chromium, and/or gold, such as for an electrical emitter or detector (e.g., an electrode) and/or one or more contact pads or wires), a dielectric (e.g., a polymer, such as any herein, as well as poly(imide), silicon oxide, silicon nitride, or alumina), a capping material (e.g., a GaAs layer), a sealant material (e.g., any described herein), etc.

These materials may be processed by any useful method. Exemplary methods include rapid prototyping, microfabrication (e.g., by casting, injection molding, compression molding, embossing, ablation, thin-film deposition, and/or Computer Numerically Controlled (CNC) micromachining), CMOS processes, deposition techniques (e.g., chemical vapor deposition (CVD)), photolithography, dicing, etching techniques (e.g., wet chemical etching, reactive ion etching (RIE), deep RIE, inductively coupled plasma deep silicon etching, laser ablation, or air abrasion techniques), singulation of a die (e.g., by dicing and trimming), etc.

Additional materials and methods of making and testing such materials are described in Abaya T V F et al., "Characterization of a 3D optrode array for infrared neural stimulation," *Biomed. Optics Exp.* 2012 September; 3(9):2200-19; Accoto D et al., "An implantable neural interface with electromagnetic stimulation capabilities," *Med. Hypoth.* 2013; 81:322-7; Brady G P et al., "Recent developments in optical fibre sensing using fibre Bragg gratings," *Proc. SPIE* 1996 October; 2839:8-19; Carboni C, "Electronic bidirectional interfaces to the peripheral nervous system for prosthetic applications," *Electronic and Computer Engineering Ph.D. thesis in the Department of Electrical and Electronic Engineering at the University of Cagliari*, March 2012 (135 pp.); Cheng H D et al., "Monolithic bi-directional linear microactuator for light beam manipulation," *IEEE/LEOS Int'l Conf on Optical MEMS and Their Applications*, held on 21-24 Aug. 2006 in Big Sky, Mont., pp. 122-3; Chiu Y et al., "MEMS-based miniature optical pickup," *IEEE Trans. Magn.* 2005 February; 41(2):967-70; Di Pino G et al., "In human implant of intraneural multielectrodes for controlling a 5-fingered hand prosthesis and delivering sensorial feedback," Chapter 3, pp. 28-38 in *Grasping the Future: Advances in Powered Upper Limb Prosthetics*, eds. V. P. Castelli and M. Troncossi, 2012, Bentham Science Publishers, Oak Park, Ill.; Di Pino G, "Bidirectional peripheral-nerve interfaces for hand prosthesis control: In human validation and analysis of the induced neuroplasticity and of the foreign body reaction," *Biomedical Engineering Ph.D. thesis in the School of Engineering at the University Campus Bio-Medico di Roma*, January 2010 (137 pp.); Garrigues M et al., "III-V semiconductor based MOEMS devices for optical telecommunications," *Microelectron. Eng.* 2002; 61-62:933-45; Hocevar M et al., "Growth and optical properties of axial hybrid III-V/silicon nanowires," *Nature Commun.* 2012 December; 3:1266 (6 pp.); Kang Y T et al., "Evaluating biocompatibility of semiconductive gallium nitride, flat and nano-structured silicon chips by cell viability, adhesion and growth," *Int'l Nanoelectronics Conf.*, held on 3-8 Jan. 2010 in Hong Kong, pp. 811-2; Kim T I et al., "Injectable, cellular-scale optoelectronics with applications for wireless optogenetics," *Science* 2013 April; 340:211-6 (including Supplementary Materials (42 pp.)); Li Y et al., "Thermal analysis of injectable, cellular-scale optoelectronics with pulsed power," *Proc. R. Soc. A.* 469:Art. no. 20130142 (13 pp.); Passaro V M N et al., "Wavelength interrogator for optical sensors based on a novel thermo-optic tunable filter in SOI," *J. Lightwave Technol.* 2012 July; 30(13):2143-50; Seo D et al., "Neural dust: An ultrasonic, low power solution for chronic brain-machine interfaces," arXiv:1307.2196v1 [q-bio.NC], 2013 July (11 pp.); Tamura K et al., "A glass-coated tungsten microelectrode enclosing optical fibers for optogenetic exploration in primate deep brain structures," *J. Neurosci. Methods* 2012; 211:49-57; Thacker H D et al., "Hybrid integration of silicon nanophotonics with 400 nm-CMOS VLSI drivers and receivers," *IEEE Electronic Components and Technology Conf.*, held on 31 May to 3 Jun. 2011 at Lake Buena Vista, Fla., pp. 829-35; Wu M C, "Micromachining for optical and optoelectronic systems," *Proc. IEEE* 1997 November; 85(11):1833-56; Cowan W D et al., "Integrated FET-polysilicon micromachining process for optical MEMS," *Proc. IEEE/LEOS Int'l Conf Optical MEMS & their Applications*, held on 2006 Aug. 21-24 in Big Sky, Mont., pp. 64-5; as well as U.S. Pub. Nos. 2011/0024771 and 2013/0245725, each of which is incorporated herein by reference in its entirety.

Circuitry and Data Processing

The active structure can include one or more circuitry, electronics, and other components. In particular, these electrical components provide electrical connections between the emitters, receivers, and detectors.

In one embodiment, the substrate of the active structure includes circuitry. The circuitry, in turn, can be connected electrically to one or more receivers, emitters, and detectors. In particular embodiments, the circuitry include one or more control electronics, components, and logic processes to encode and decode an electrical signal, record one or more signals, apply an algorithm to an electrical signal into an electrical input for emitter(s) and/or detector(s), store power, and/or transmit power. Such control electronics can be configured to allow for current-controlled and voltage-controlled electrical signals for intra-nodal transmission or transmission between a node and the target.

In another embodiment, the circuitry includes signal processing circuitry that is configured to receive one or more electrical signals from at least one detector, apply an algorithm to the electrical signal(s) to provide one or more processed electrical signals, and transmit the processed electrical signal(s) to at least one emitter, where the emitter is configured to convert the processed electrical signal(s) to the target optical input or target electrical input for transmission to the biological target.

The incoming data and outgoing data could be encoded in slightly different wavelengths (wavelength division) or other means (by code-division multiple access or time-division multiple access, other encoding schemes). This allows extremely high bandwidth connections to the nodes and therefore to the neural tissue.

The circuitry can be powered by any useful means. For instance, the circuitry can be connected electrically to one or more power photodiodes for receiving power that is optically transmitted down the fiber by the external unit. In addition, the circuitry can be configured to receive electrical output from the power diodes and condition it for use by the other integrated circuit elements. In another instance, the active structures or nodes may further include storage elements, such as capacitors, for accumulating energy output by the power photodiodes over relatively long intervals and releasing it in pulses as required.

The circuitry can include any other electronic or optoelectronic components beneficial for signal processing and storage. Such components include low noise amplifiers, preamplifiers, filters, modulators, analog-to-digital converters, digital-to-analog converters, V/I converters, etc. Exemplary circuitry and components are described in Carboni C, "Electronic bidirectional interfaces to the peripheral nervous system for prosthetic applications," *Electronic and Computer Engineering Ph.D. thesis in the Department of Electrical and Electronic Engineering at the University of Cagliari*, March 2012 (135 pp.), Huang C W et al., "Electrochemical detection of the neurotransmitter dopamine by nanoimprinted interdigitated electrodes and a CMOS circuit with enhanced collection efficiency," *IEEE Sensors J.* 2011 September; 11(9):1826-31, as well as U.S. Pub. Nos. 2009/0177144, 2009/0210039, and 2014/0094674, and Int. Pub. No. WO 2010/042750, each of which is incorporated herein by reference in its entirety.

External Transceiver Unit, Power Unit, and Processing Units

One or more external units can be coupled to the active structure(s), as well as apparatuses and devices having such active structures. The external unit can be configured to provide an external optical input, which is relayed to the coupling nodes. The external unit can be further configured to communicate with other external components, including one or more of the following: power units, processing units, artificial prostheses, etc.

Figure 6:
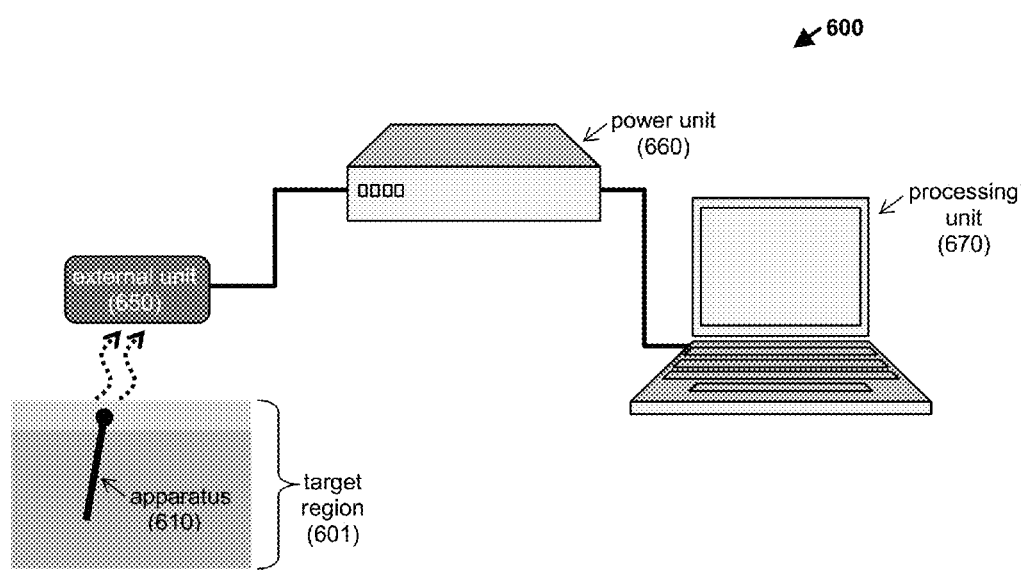
FIG. 6 provides a schematic of a system 600 including an apparatus 610, an external transceiver unit 650, an external power unit 660, and an external processing unit 670.

FIG. 6 provides an exemplary system 600 in which an external unit 650 is receiving transcutaneous optical transmissions from an apparatus 610 subcutaneously embedded in the target region 601 of a subject. As seen in the figure, a power and signal conditioning unit 660 controls an external optical transceiver unit, and relays data signals between the transceiver unit 650 and a unit for signal processing and input-output 670.

As described herein, the apparatuses of the invention includes one or more active structures or nodes to record and stimulate neuronal interfaces. Accordingly, one or more external components can be present to transmit recording and stimulation data, e.g., implantable multiplexed optical interconnects (e.g., using one or more photodetectors, photoemitters, or receivers, such as any herein), implantable reconfigurable low-power signal processing to compress and en/decrypt data, implantable wireless data transceivers, and implantable power receivers. In addition, to further ease use, one or more of the external units can be portable and/or wearable, as well as include wireless transmitting and receiving capabilities. Exemplary external units and feedback systems are described in U.S. Pat. No. 7,729,773 and U.S. Pub. No. 2009/0118800, each of which is incorporated herein by reference in its entirety.

In at least some implementations, it will be advantageous to employ multiplexing techniques so that, for example, downstream messages can be individually addressable to respective terminals, and upstream messages can likewise be attributed to individual, respective terminals. Any of various multiplexing techniques are available for such purpose, including wavelength multiplexing, code multiplexing, time multiplexing, and radio frequency multiplexing.

It should be noted in this regard that neural data rates are typically in the kilohertz range. If it is desired to transmit enough information to reproduce, e.g., an entire action potential waveform, a transmission bandwidth of several tens of kHz per neuron is sufficient. If hundreds of neurons are to be probed, a total signal bandwidth of several megahertz per optical fiber would therefore suffice. Of course if only selected, derived features of the neural waveform are to be transmitted, substantially lower signal bandwidths may suffice. Any of various modulation schemes will be useful in this regard. One example is frequency modulation, which may be advantageous because it can provide high signal-to-noise ratios and is relatively simple to implement.

Uses and Methods

The structures, devices, apparatuses, and systems of the invention can be used for any useful purpose, such as detecting and/or treating a biological target. In particular embodiments, the method includes implanting or injecting the structures or devices of the invention in the target region (e.g., a neural tissue, such as in a peripheral nerve or a central nerve) for real-time, in vivo monitoring and control. Other exemplary target regions include a tissue (e.g., neural tissue, neural fascicles, subcutaneous tissue, muscle, nerve, peripheral nerve, central nerve, etc.), a cell (e.g., a neuron, a muscle cell, or a glial cell), an organ (e.g., brain), etc.

There are tissue transmission windows in which light can be delivered with minimal absorption and scattering in these specific wavelength ranges. This range can be chosen to be sufficiently away from the wavelengths at which the light sensitive molecules operate, either for stimulation or activity reporting (action potentials, other chemical, physiological states).

For optical transmission within the biological medium, it is important to find a spectral window that offers sufficient transparency. In one embodiment, the spectral window is any range or ranges of from about 600 nm to about 1300 nm. Optical transmission depends on numerous factors, including the wavelength of the external optical input, desired tissue penetration depth, the presence of one or more components in the epidermis (e.g., melanin), and/or the presence of one or more chromophores in the dermis (e.g., bilirubin, hemoglobin, oxyhemoglobin, etc.). In general, longer wavelength optical signals penetrate deeper into the skin tissue (e.g., about 1.2 mm for 800 nm light). In addition, whereas the presence of absorbing components is a major consideration to penetrate the epidermis, tissue turbidity and optical scattering are the major consideration for optical radiation of the dermis. Various studies, models, and data are provided in Tuchin V V, "Light scattering study of tissues," *Phys. Uspekhi* 1997; 40(5):495-515; and Anderson R R et al., "The optics of human skin," *J. Invest. Dermatol.* 1981; 77:13-9, each of which is incorporated herein by reference in its entirety. Based on these teachings, a skilled artisan would be able to choose the appropriate wavelength for the external optical input signal based on the location of the apparatus or structure in the target region.

One such optical window within, e.g., human, tissue lies in the vicinity of 633 nm. In one illustrative scenario, an optical power feed at or near 633 nm and with 50 mW optical power is emitted from an external source. We estimate that 45 mW may be coupled into the implanted fiber, and that of that total, 5 mW may be delivered to each of, e.g., eight nodes. With high conversion efficiency, this could make 4 mW of electrical power available to each node. That would be enough power to run a circuit of sufficient complexity to provide useful functions. For burst mode operation, requiring more power, the energy from the power cell could be integrated over a timescale of, e.g., ten seconds and released over a shorter timescale to provide several tens of milliwatts of burst-mode power. It should also be noted in this regard that penetrating, non-optical methods of wireless power delivery may also be available, such as microwave power transmission power delivery through inductive coupling.

Other uses include control of external, artificial prostheses and other assistive technologies by combining the optoelectronic structures, devices, and systems of the invention to provide tactile and proprioceptive feedback between the user and the prosthesis or other mechtronic or robotic external devices. Any of the structures and systems herein can be used to provide bidirectional telemetry between the implanted apparatus and these external devices. Exemplary prostheses and related methods are described in Cipriani C et al., "Objectives, criteria and methods for the design of the SmartHand transradial prosthesis," *Robotica* 2010; 28:919-27; Micera S et al., "Control of hand prosthesis using peripheral information," *IEEE Rev. Biomed. Eng.* 2010; 3:48-68; Rossini P M et al., "Double nerve intraneural interface implant on a human amputee for robotic hand control," *Clin. Neurophysiol.* 2010; 121:777-83; and Cipriani C et al., "The SmartHand transradial prosthesis," *J. Neuroeng. Rehab.* 2011 May; 8:29 (13 pp.), each of which is incorporated herein by reference in its entirety.

Another exemplary use includes studies requiring optogenetics, which includes genetic modifications to provide optically addressable cells. Such genetic modifications can include genetically modified cells, enzymes, lipids, and/or proteins. By applying the optoelectronic structures, devices, and systems of the invention, studies can be conducted in test subjects (e.g., animal test subjects) to understand various biological and biochemical mechanisms underlying nerve damage, regeneration, and control. Exemplary genetic modifications include injection of an engineered virus (e.g., a rabies virus) encoding a fluorescent protein (e.g., EGFP) to label neurons, activity-dependent expression of opsin-conjugated fluorescent proteins (e.g., channelrhodopsin (ChR2) conjugated with gfEYFP), GFP reconstitution across synaptic partners (GRASP), chimeric-opsin formation, in vivo expression of $Ca^{2+}$ indicator proteins (e.g., GCaMP3), and addition of membrane trafficking tags. Additional optogenetic methods and genetic modifications are described in Chung K et al., "CLARITY for mapping the nervous system," *Nature Methods* 2013 June; 10(6):508-13; Deisseroth K et al., "Engineered approaches to illuminating brain structure and dynamics," *Neuron* 2013 October; 80:568-77; Mattis J et al., "Principles for applying optogenetic tools derived from direct comparative analysis of microbial opsins," *Nature Methods* 2012 February; 9(2):159-172 (including 3 pp. of Online Methods); and Chung K et al., "Structural and molecular interrogation of intact biological systems," *Nature* 2013 May; 497:332-7; as well as U.S. Pat. Nos. 6,662,039, 8,398,692, 8,603,790, and 8,696,722, and U.S. Pub Nos. 2010/0292931 and 2013/0224756, each of which is incorporated herein by reference in its entirety.

Yet another exemplary application is deep brain stimulation (DBS), which is already being used for treating Parkinson's or other neurological problems with electrical stimulation. This approach would provide much higher level of control and customizability.

Further uses include treatment of diseases and conditions requiring stimulation of peripheral and/or central nerves, such as treatment of neurogenic pain, diabetic neuropathy, phantom limb syndrome in amputees (e.g., in its thalamic, peripheral and/or central component), spasticity, dystonia, tremor, Parkinson's disease, multiple sclerosis, epilepsy, vision disorders, and movement disorders. Other potential uses are described in Smedemark-Margulies N et al., "Tools, methods, and applications for optophysiology in neuroscience," *Front. Molec. Neurosci.* 2013 July; 6:18 (13 pp.), which is incorporated herein by reference in its entirety.

Other Embodiments

All publications, patents, and patent applications, including U.S. Provisional Application No. 61/839,264, filed Jun. 25, 2013, mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. Apparatus comprising a biological probe active structure and an optical connector having a proximal end and a distal end, wherein:
   the biological probe active structure comprises an implantable hermetically sealed unit and an optically transparent bonding structure that attaches the hermetically sealed unit to the distal end of the optical connector and facilitates an optical connection of the optical connector to the hermetically sealed unit,
   the hermetically sealed unit comprises one or more emitters disposed on a substrate, wherein at least one emitter is configured to transmit a target input to a biological target and wherein the target input is a first optical and/or electrical signal;
   the hermetically sealed unit further comprises one or more detectors disposed on the substrate, wherein at least one detector is configured to receive a target output from the biological target and wherein the target output is a second optical and/or electrical signal;
   the hermetically sealed unit further comprises a signal processor circuitry disposed on the substrate and coupled electrically to the one or more emitters and the one or more detectors;
   the hermetically sealed unit further comprises a power component disposed on the substrate and configured to receive external optical power and provide internal electrical power for use by other elements disposed on the substrate;
   the optical connector is an optical fiber,
   the apparatus further comprises an optical collector connected to the proximal end of the optical fiber; and
   the power component is disposed so as to receive the external optical power from the optical fiber through the optically transparent bonding structure.

2. The apparatus of claim 1, wherein the signal processor circuitry is configured to receive one or more electrical signals from at least one detector within the probe active structure, apply an algorithm to the electrical signal(s) to provide one or more processed electrical signals, and transmit the processed electrical signal (a) to at least one emitter within the probe active structure, wherein the emitter(s) is configured to convert the processed electrical signal(s) to one or more optical signals as the target input for transmission to the biological target.

3. The apparatus of claim 1, wherein the biological probe active structure is a self-contained single module configured to be embedded in a target region, and wherein the biological probe active structure is configured to transmit the one or more target inputs directly into the target region and to receive one or more target outputs directly from the same target region.

4. The apparatus of claim 1, further comprising an ionic layer and/or a modulation layer disposed on a peripheral surface of the hermetically sealed unit.

5. The apparatus of claim 4, wherein the ionic layer and/or the modulation layer comprises a light-activated material, an optically interrogatable material, a detection material, or a photo missive material.

6. The apparatus of claim 4, wherein the ionic layer comprises a material configured to alter and/or detect a local ionic concentration upon activation.

7. The apparatus of claim 6, wherein the activation comprises stimulating and/or suppressing cellular activity in the target region.

8. The apparatus of claim 4, wherein the modulation layer comprises a material configured to alter and/or detect a local modulator concentration upon activation.

9. The apparatus of claim 1, comprising:
   a plurality of coupling nodes, wherein each coupling node comprises at least one said biological probe active structure, and each coupling node is connected optically to the distal end of the connector.

10. The apparatus of claim 9, wherein the optical connector is configured to transmit an external optical input to the coupling node(s) and to receive one or more relayed optical outputs from the coupling node(s).

11. The apparatus of claim 10, wherein the apparatus comprises two or more optical connectors.

12. The apparatus of claim 11, further comprising a first optical connector that comprises a plurality of first coupling nodes and a second optical connector that comprises a plurality of second coupling nodes, wherein at least one first coupling node is configured to communicate electrically and/or optically with at least one second coupling node.

13. The apparatus of claim 9, wherein the optical collector is a lens configured to receive one or more external optical inputs from an external transceiver unit.

14. The apparatus of claim 13, further comprising a reflector disposed on a surface of the collector.

15. The apparatus of claim 9, wherein the optical connector comprises an internal scattering structure or an optical tap configured to split an external optical input into one or more optical input signals.

16. The apparatus of claim 15, wherein each coupling node is arrayed along the optical connector near the scattering structure or tap, such that a portion of the light incident on each scattering structure or tap is coupled into a corresponding coupling node.

17. The apparatus of claim 9, wherein the collector is configured for in vivo implantation or injection in a target region.

18. The apparatus of claim 17, target region is a subcutaneous region in an organism.

19. The apparatus of claim 18, further comprising an external transceiver unit configured to receive and transmit transcutaneous signals to and from the collector.

20. A system comprising the apparatus of claim 9 and further comprising:
an external transceiver unit configured to transmit one or more external optical inputs to the apparatus via the optical connector and configured to receive one or more injected optical outputs from the apparatus, at least one external optical input being an optical power input received by the one or more power photodetectors for providing internal electrical power for use by other elements disposed on a substrate.

21. The system of claim 20, further comprising a power unit configured to be connected to the external transceiver unit and a processing unit configured to be connected to the power unit.

22. The structure of claim 1, wherein the power component comprises one or more power photodetectors.

23. The structure of claim 22, the power component further comprising a storage element for accumulating energy output by the one or more power photodetectors over a relatively long time interval.

24. A method of detecting and/or treating a biological target, the method comprising:
providing one or more external optical inputs to an apparatus comprising one or more biological probe active structures and an optical fiber having a proximal end and a distal end, and receiving one or more injected optical outputs from the apparatus, wherein:
each biological probe active structure comprises an implantable hermetically sealed unit and an optically transparent bonding structure that attaches the hermetically sealed unit to the distal end of the optical fiber and facilitates an optical connection of the optical fiber to the hermetically sealed unit;
the apparatus comprises a plurality of coupling nodes, wherein each coupling node comprises one or more biological probe active structures and each coupling node is connected optically to the distal end of the optical fiber;
each hermetically sealed unit comprises one or more emitters disposed on a substrate, wherein at least one emitter is configured to transmit a target input to a biological target and wherein the target input is a first optical and/or electrical signal;
each hermetically sealed unit further comprises one or more detectors disposed on the substrate, wherein at least one detector is configured to receive a target output from the biological target and wherein the target output is a second optical and/or electrical signal;
each hermetically sealed unit comprises a signal processing circuitry disposed on the substrate and coupled electrically to the one or more emitters and the one or more detectors;
each hermetically sealed unit comprises one or more power photodetectors disposed on the substrate;
the apparatus further comprises an optical collector connected to the proximal end of the optical fiber;
and wherein the providing one or more external optical inputs to the apparatus comprises using an external transceiver unit to transmit the one or more external optical inputs to the apparatus via the optical collector and the optical fiber;
and wherein the receiving one or more injected optical outputs from the apparatus comprises using the external transceiver unit to receive the one or more injected optical outputs from the apparatus;
and wherein the providing one or more external optical inputs to the apparatus further comprises providing, on at least one external optical input, an optical power input received by the one or more power photodetectors from the optical fiber through an optically transparent bonding structure for providing internal electrical power for use by other elements disposed on the substrate.

25. The method of claim 24, further comprising receiving one or more injected optical outputs transmitted from the apparatus.

26. The method of claim 25, wherein an external transceiver unit is configured to transmit the external optical input(s) to the apparatus and to receive the injected optical output(s) from the apparatus.

* * * * *